US011045793B1

United States Patent
Soliman et al.

(10) Patent No.: US 11,045,793 B1
(45) Date of Patent: Jun. 29, 2021

(54) CONTROLLED ON-POT DESIGN OF MIXED COPPER/ZINC OXIDES SUPPORTED ALUMINUM OXIDE AS AN EFFICIENT CATALYST FOR CONVERSION OF SYNGAS TO HEAVY LIQUID HYDROCARBONS AND ALCOHOLS UNDER AMBIENT CONDITIONS FEASIBLE FOR THE FISCHER-TROPSCH SYNTHESIS

(71) Applicant: QATAR UNIVERSITY, Doha (QA)

(72) Inventors: Ahmed Mohamed Shehata Soliman, Alexandria (EG); Kamel Abdelmoniem Mohamed Eid, Sharkia (EG); Aboubakr Moustafa Abdullah, Giza (EG); Ahmed Abdelfattah Ahmed Mohamed Elzatahry, Nabeel-Altwabik-Faisal (EG)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 16/938,848

(22) Filed: Jul. 24, 2020

(51) Int. Cl.
*B01J 23/80* (2006.01)
*B01J 21/04* (2006.01)
(Continued)

(52) U.S. Cl.
CPC ............... *B01J 23/80* (2013.01); *B01J 21/04* (2013.01); *B01J 35/08* (2013.01); *B01J 37/0027* (2013.01);
(Continued)

(58) Field of Classification Search
CPC ... B01J 21/04; B01J 21/18; B01J 23/80; B01J 35/08; B01J 35/0073; B01J 37/0027;
(Continued)

(56) References Cited

U.S. PATENT DOCUMENTS 3,850,850 A * 11/1974 Collins ................. C07C 29/154
502/307
4,279,781 A * 7/1981 Dienes ..................... B01J 23/80
502/343
(Continued)

FOREIGN PATENT DOCUMENTS

GB          1 131 631    * 10/1968 .............. B01J 11/22
KR    2008-0011628 A      2/2008
(Continued)

OTHER PUBLICATIONS

Al-Dossary, et al: "Cu-promoted Fe2O3/MgO-based Fischer-Tropsch catalysts of biomass-derived syngas", Industrial & Engineering Chemistry Research 2015; published Dec. 30, 2014, vol. 54(3): pp. 911-921.
(Continued)

*Primary Examiner* — Patricia L. Hailey
(74) *Attorney, Agent, or Firm* — Squire Patton Boggs (US) LLP

(57) ABSTRACT

Set forth herein is a Fischer-Tropsch catalytic system that allows for the efficient and selective conversion of syngas to useful hydrocarbons ($nC_4$-$nC_{24}$) as well as heavy alcohols ($nC_1$-$nC_9$) under ambient conditions. The instantly disclosed catalytic system is more practical and scalable than other known Fischer-Tropsch catalytic systems. Also set forth herein new catalysts which comprise supported metal-oxide-based catalysts. These catalysts are useful for the conversion of syngas into liquid hydrocarbon fuels under ambient reaction conditions. The instantly disclosed catalytic system can be made in a one-pot high mass production method, which is commercially practical and scalable. A variety of reaction products can be produced by making minor adjustments to the processes disclosed herein, e.g., by adjusting catalyst composition, reaction temperature and/or reaction pressure. The instantly disclosed process(es) produce Fis-
(Continued)

cher-Tropsch products, heavy hydrocarbons (e.g., paraffin's, olefins, and their derivatives), and alcohols.

19 Claims, 34 Drawing Sheets

(51) Int. Cl.
| | |
|---|---|
| B01J 35/08 | (2006.01) |
| B01J 37/08 | (2006.01) |
| C10G 2/00 | (2006.01) |
| B01J 37/00 | (2006.01) |
| B82Y 40/00 | (2011.01) |
| B82Y 30/00 | (2011.01) |
| B01J 21/18 | (2006.01) |
| B01J 35/00 | (2006.01) |

(52) U.S. Cl.
CPC .............. B01J 37/08 (2013.01); C10G 2/33 (2013.01); *B01J 21/18* (2013.01); *B01J 35/0073* (2013.01); *B82Y 30/00* (2013.01); *B82Y 40/00* (2013.01); *C01P 2006/80* (2013.01)

(58) Field of Classification Search
CPC . B01J 37/08; C10G 2/33; B82Y 30/00; B82Y 40/00; C01P 2006/80
USPC .................. 502/341, 342, 345, 355; 518/713
See application file for complete search history.

(56) References Cited

U.S. PATENT DOCUMENTS

| | | | | |
|---|---|---|---|---|
| 4,547,482 | A * | 10/1985 | Osugi | B01J 27/1817 |
| | | | | 502/183 |
| 4,565,803 | A * | 1/1986 | Schoenthal | B01J 23/80 |
| | | | | 502/303 |
| 5,523,326 | A * | 6/1996 | Dandekar | C07C 5/2772 |
| | | | | 518/702 |
| 6,147,125 | A * | 11/2000 | Shikada | B01J 23/06 |
| | | | | 518/713 |
| 6,638,892 | B1 | 10/2003 | Wu et al. | |
| 6,800,665 | B1* | 10/2004 | Shikada | B01J 21/04 |
| | | | | 518/700 |
| 9,126,876 | B2 | 9/2015 | De Jong et al. | |
| 10,066,169 | B2 | 9/2018 | Bae et al. | |
| 10,190,057 | B2 | 1/2019 | Walsh et al. | |
| 2004/0122267 | A1* | 6/2004 | Sher | C01B 3/386 |
| | | | | 585/324 |
| 2007/0281203 | A1* | 12/2007 | Kobayashi | B01J 37/03 |
| | | | | 252/373 |
| 2008/0033218 | A1* | 2/2008 | Lattner | C07C 11/02 |
| | | | | 568/897 |
| 2009/0149324 | A1* | 6/2009 | Madon | B01J 35/0053 |
| | | | | 502/342 |
| 2010/0222624 | A1* | 9/2010 | Fujimoto | B01J 29/7415 |
| | | | | 585/733 |
| 2013/0210612 | A1* | 8/2013 | Schafer | C07C 41/01 |
| | | | | 502/71 |

FOREIGN PATENT DOCUMENTS

| | | |
|---|---|---|
| KR | 10-0859743 B1 | 9/2008 |
| KR | 2009-0011459 A | 2/2009 |
| WO | WO 2013/120711 A1 | 8/2013 |

OTHER PUBLICATIONS

Boller, et al: "The active sites of a working Fischer-Tropsch catalyst revealed by operando scanning tunnelling microscopy", Nature Catalysis Articles 2019; vol. 2(11): pp. 1027-1034.

Calderone, et al: "De novo design of nanostructured iron-cobalt Fischer-Tropsch catalysts", Core Shell Catalysts; Agnew. Chem. Int. Ed 2013; vol. 52(16): pp. 4397-4401.

Chen, et al: "Effect of tetrahedral aluminum on the catalytic performance of Al—SBa-15 supported Ru catalysts in Fischer-Tropsch synthesis", Catalysis Science & Technology, The Royal Society of Chemistry 2013; vol. 3(4): pp.

Chen, et al: "Ru catalysts supported on Al—SBa-15 with high aluminum content and their bifunctional catalytic performance in Fischer-Tropsch synthesis", Catalysis Science & Technology, The Royal Society of Chemistry 2014; vol. 4(4): pp. 1005-1011.

Chen, et al: "ZSM-5 seed-grafted SBa-15 as a high performance support for cobalt Fischer-Tropsch synthesis catalysts", Catalysis Science & Technology, The Royal Society of Chemistry 2015; vol. 5(11): pp. 4985-4990.

Das, et al: "Fischer-Tropsch synthesis: Kinetics and effect of water for a Co/SiO2 catalyst", Energy & Fuels, American Chemical Society, Apr. 21, 2005; vol. 19(4): pp. 1430-1439.

Enger, et al: "Effects of Sulphur on a Co/Mn-based Catalyst for Fischer-Tropsch Reactions", Catalysis Letters, Aug. 28, 2018; vol. 148(10): pp. 2980-2991.

Eschemann, et al: "Effects of noble metal promotion for Co/TiO2 Fischer-Tropsch catalysts", Catalysis Today 2016—available online Aug. 13, 2015; vol. 261: pp. 60-66.

Jahangiri, et al: "A review of advanced catalyst development for Fischer-Tropsch synthesis of hydrocarbons from biomass derived syn-gas", Catalysis Science & Technology, the Royal Society of Chemistry 2014; vol. 4(8): pp. 2210-2229.

Kizilkaya, et al: "Effect of ammonia on cobalt Fischer-Tropsch synthesis catalysts: a surface science approach", Catalysis Science & Technology, the Royal Society of Chemistry 2019; vol. 9(3): pp. 702-710.

Liu, et al: "Promotion effects of plasma treatment on silica supports and catalyst precursors for cobalt Fischer-Tropsch catalysts", RSC Advances 2016; vol. 6(62): pp. 57701-57708.

Liu, et al: "Effect of TiO2 Surface Engineering on the Performance of Cobalt-Based Catalysts for Fischer-Tropsch Synthesis", Industrial & Engineering Chemistry Research, Dec. 20, 2018; vol. 58(2): pp. 1095-1104.

Lok: "Novel highly dispersed cobalt catalysts for improved Fischer-Tropsch productivity", Studies in Surface Science and Catalysis 2004; vol. 147, pp. 283-288.

Lyu, et al: "Structural evolution of carbon in an Fe@ C catalyst during the Fischer-Tropsch synthesis reaction", Science and Technolgy manuscript, Catalysis, Royal Society of Chemistry 2019; vol. 9(4): pp. 1013-1020.

Ma, et al: "Fischer-Tropsch Synthesis over Activated-Carbon-Supported Cobalt Catalysts: Effect of Co Loading and Promoters on Catalyst Performance", Ind. Eng. Chem, Apr. 15, 2004; vol. 43(10): pp. 2391-2398.

Mahmoudi, et al: "A review of Fischer Tropsch synthesis process, mechanism, surface chemistry and catalyst formulation", Biofuels Eng. 2017; vol. 2(1): pp. 11-31.

Nieskens, et al: "Production of light hydrocarbons from syngas using a hybrid catalyst", Inustrial & Engineering Chemistry Research 2017; vol. 56(10): pp. 2722-2732.

Oukaci, et al: "Comparison of patented Co F—T catalysts using fixed-bed and slurry bubble column reactors", Applied Catalysis 1999; vol. 186(1-2): pp. 129-144.

Riyahin, et al: "Optimization of reaction condition on the product selectivity of Fischer-Tropsch synthesis over a Co—SiO2/SiC catalyst using a fixed bed reactor", Petroleum Science and Technology, Sep. 11, 2017; vol. 35(11): pp. 1078-1084.

Sadek, et al: "Cobalt Based Catalysts Supported on Two Kinds of Beta Zeolite for Application in Fischer-Tropsch Synthesis",Catalysts, May 29, 2019; vol. 9(6): p. 497.

Shafer, et al: "Fischer-Tropsch: Product Selectivity—The Fingerprint of Synthetic Fuels", Catalysts, Mar. 14, 2019; vol. 9(3): p. 259.

Smiley, et al: "Fischer-Tropsch Snythesis: Comparisons of SiO2 and SiC-supported Co catalysts prepared through aqueous impregnation and CVD methods, Fischer-Tropsch Synthesis, Catalysts, and Cataly-

(56) References Cited

OTHER PUBLICATIONS sis", 2016, CRC Press, downloaded from the University of Michigan Library (Ann Arbor, Flint & Dearborn) Jul. 17, 2016; pp. 74-103.
Sun, et al: "Novel Cobalt Catalysts Supported on Metal—Organic Frameworks MIL-53 (Al) for the Fischer-Tropsch Synthesis", Energy Technology Generation, Conversion, Storage, Distribution, Energy Technology 2019, Full Paper; vol. 7(4): p. 1800802.
Torres, et al: "Catalysts for production of lower olefins from synthesis gas: a Review", Catalysis, Jul. 8, 2013, American Chemical Society; vol. 3(9): pp. 2130-2149.
Van De Loosdrecht, et al: "Fischer-Tropsch synthesis: catalysts and chemistry", Comprehensive Inorganic Chemistry II: from elements to applications, Elsevier 2013; pp. 525-557.
Van Deelen, et al: "Preparation of Cobalt nanocrystals supported on metal oxides to study particle growth in Fischer-Tropsch catalysts", Catalysis, Oct. 5, 2018; vol. 8(11): pp. 10581-10589.
Van Helden, et al: "Cobalt-nickel bimetallic Fischer-Tropsch catalysts: A combined theoretical and experimental approach", Catalysis Today 2020; vol. 342: pp. 88-98.
Venvik, et al: "Catalysis in microstructured reactors: Short review on small-scale syngas production and further conversion into methanol, DME and Fischer-Tropsch products", Catalysis Today, Feb. 21, 2017; vol. 285: pp. 135-146.
Wang, et al: "Improved Fischer-Tropsch synthesis for gasoline over Ru, Ni promoted Co/HZSM-5 catalysts", Fuel 2013; vol. 108: pp. 597-603.
Wei, et al: "Fischer-Tropsch Synthesis Bifunctional Catalysts: Cobalt Supported on 3D Mesoporous Cellular Silica Foams Assembled by Using ZSM-5 Seed", Heterogeneous & Homogeneous & Bio- & Nano—CatChemCat Catalysis 2017; vol. 9(20): pp. 3895-3903.
Xiong, et al: "Preparation and catalytic activity for Fischer-Tropsch synthesis of Ru Nanoparticles confined in the channels of mesoporous SBA-15", Journal of Physical Chemistry 2008; vol. 112(26): pp. 9706-9709.
Yunes, et al: "Effect of High Pressure on the Reducibility and Dispersion of the Active Phase of Fischer-Tropsch Catalysts", Materials, Jun. 13, 2019; vol. 12(12): p. 1915.
Zamani, et al: "Effect of Calcium Promoters on Nanostructured Iron Catalyst for Fischer-Tropsch Synthesis", Journal of Petroleum Science and Technology, Feb. 10, 2015; vol. 5(1): pp. 21-27.
Zhao, et al: "SBA-16-Supported Cobalt Catalyst with High Activity and Stability for Fischer-Tropsch Synthesis", Full Papers , ChemCatChem 2012; vol. 4(2): pp. 265-272.

* cited by examiner

CONTROLLED ON-POT DESIGN OF MIXED COPPER/ZINC OXIDES SUPPORTED ALUMINUM OXIDE AS AN EFFICIENT CATALYST FOR CONVERSION OF SYNGAS TO HEAVY LIQUID HYDROCARBONS AND ALCOHOLS UNDER AMBIENT CONDITIONS FEASIBLE FOR THE FISCHER-TROPSCH SYNTHESIS

FIELD

The present disclosure concerns catalysts for the conversion of syngas to hydrocarbons.

BACKGROUND

Production of gasoil, kerosene and base oil to naphtha and normal paraffins from oil, gas, and coal occurs primarily through the Fischer-Tropsch process (FTs). Much work has been dedicated to developing catalytic-systems for FTs. This work resulted in Co-based, Fe-based, and Ru-based catalysts, which varied in their performances and conditions. For example, there are reports Cu/Zn-based catalysts for the production of dimethyl ether although not for the production of heavy liquid hydrocarbons and alcohols, through the fixed bed rector. Others have used carbon-based and metal-oxides catalysts and/or their composites for FTs. However, these compositions and processes are limited.

What is needed are new, efficient catalytic systems, processes, and catalysts for Fischer-Tropsch reactions and other new catalysts for gas to liquid (GTL) reactions which can replace the cobalt-based and iron-based catalysts currently used today. Set forth herein are solutions to this as well as other relevant problems in the field to which the instant disclosure pertains.

SUMMARY

In one embodiment, set forth herein is a composition comprising CuO and ZnO on $Al_2O_3$, wherein the composition comprises: 35 to 80 percent by mole CuO; 25 to 35 percent by mole ZnO; and 5 to 15 percent by mole $Al_2O_3$; wherein the total percent by mole amount of Cu, ZnO, and $Al_2O_3$ is 100.

In another embodiment, set forth herein is a process for making CuO/ZnO supported on $Al_2O_3$ comprising: combusting metal precursors, glycine and water to form a powder; and annealing the powder; wherein the metal precursors are selected from the group consisting of $Cu(NO_3)_2$, $Zn(NO_3)_2$, and $Al(NO_3)_2$.

A process for converting syngas into usable liquid hydrocarbons (e.g., $nC_4$-$nC_{24}$ and $nC_1$-$nC_9$) alcohols comprising contacting syngas to a catalyst set forth herein, under syngas reaction conditions.

BRIEF DESCRIPTIONS OF THE DRAWINGS

FIG. 1(a), FIG. 1(b), and FIG. 1(c) each show scanning electron microscope (SEM) images of $CuO_{(40)}/ZnO_{(30)}/Al_2O_{3(30)}$ catalysts prepared using Cu/Zn with atomic ratios of 1/1. FIG. 1(d) shows the associated electron dispersive x-ray (EDX) analysis.

FIG. 2(a), FIG. 2(b), and FIG. 2(c) each show SEM images of $CuO_{(60)}/ZnO_{(30)}/Al_2O_3(10)$ prepared using Cu/Zn with a ratio of 1.66/1, respectively. FIG. 2(d) shows the associated EDX analysis.

FIG. 3(a), FIG. 3(b), and FIG. 3(c) each show SEM images of $CuO_{(75)}/ZnO_{(15)}/Al_2O_{3(10)}$ prepared using Cu/Zn with a ratio of 4/1, respectively.

FIG. 4 shows an x-ray diffraction patter for catalysts prepared according to the instant disclosure with comparison to pure $Al_2O_3$ particles.

FIG. 5(a), FIG. 5(b), FIG. 5(c), and FIG. 5(d) each show high-resolution x-ray photoelectron spectroscopy (XPS) of the as-synthesized catalysts for Cu, Zn, and O 1s, respectively. The $CuO_{(40)}/ZnO_{(30)}/Al_2O_{3(30)}$ including catalysts were prepared under the conditions set forth herein.

FIG. 6(a), FIG. 6(b), and FIG. 6(c) each show high-resolution XPS spectra of $CuO_{(60)}/ZnO_{(30)}/Al_2O_{3(10)}$ catalyst of Cu 2p, Zn 2p, and O 1s, respectively.

FIG. 7(a), FIG. 7(b), and FIG. 7(c) each show high-resolution XPS spectra of $CuO_{(75)}/ZnO_{(15)}/Al_2O_{3(10)}$ catalyst of Cu 2p, Zn 2p, and O 1s, respectively.

FIG. 8A, FIG. 8B, FIG. 8C, FIG. 8D, FIG. 8E, and FIG. 8F, each show GC-FID analysis for the liquid products obtained using $CuO_{(40)}/ZnO_{(30)}/Al_2O_{3(30)}$ catalysts at 250° C. and under 50 bar, respectively.

FIG. 9A, FIG. 9B, FIG. 9C, FIG. 9D, FIG. 9E, and FIG. 9F, each show GC-FID analysis carried out for the liquid products obtained using $CuO_{(60)}/ZnO_{(30)}/Al_2O_{3(10)}$ supported on $Al_2O_3$ catalysts at 250° C. and under 50 bar.

FIG. 17 (a) shows GC-Ms analysis carried out for the liquid products obtained using $CuO_{(75)}/ZnO_{(15)}/Al_2O_{3(10)}$ supported on $Al_2O_3$ catalysts at 250° C. and under 70 bar. FIGS. 17(b) and 17 (c) show the magnification of the area with relation to alcohols. FIG. 17 (d) shows the confirmation by the GC-FID results.

Figure 18:
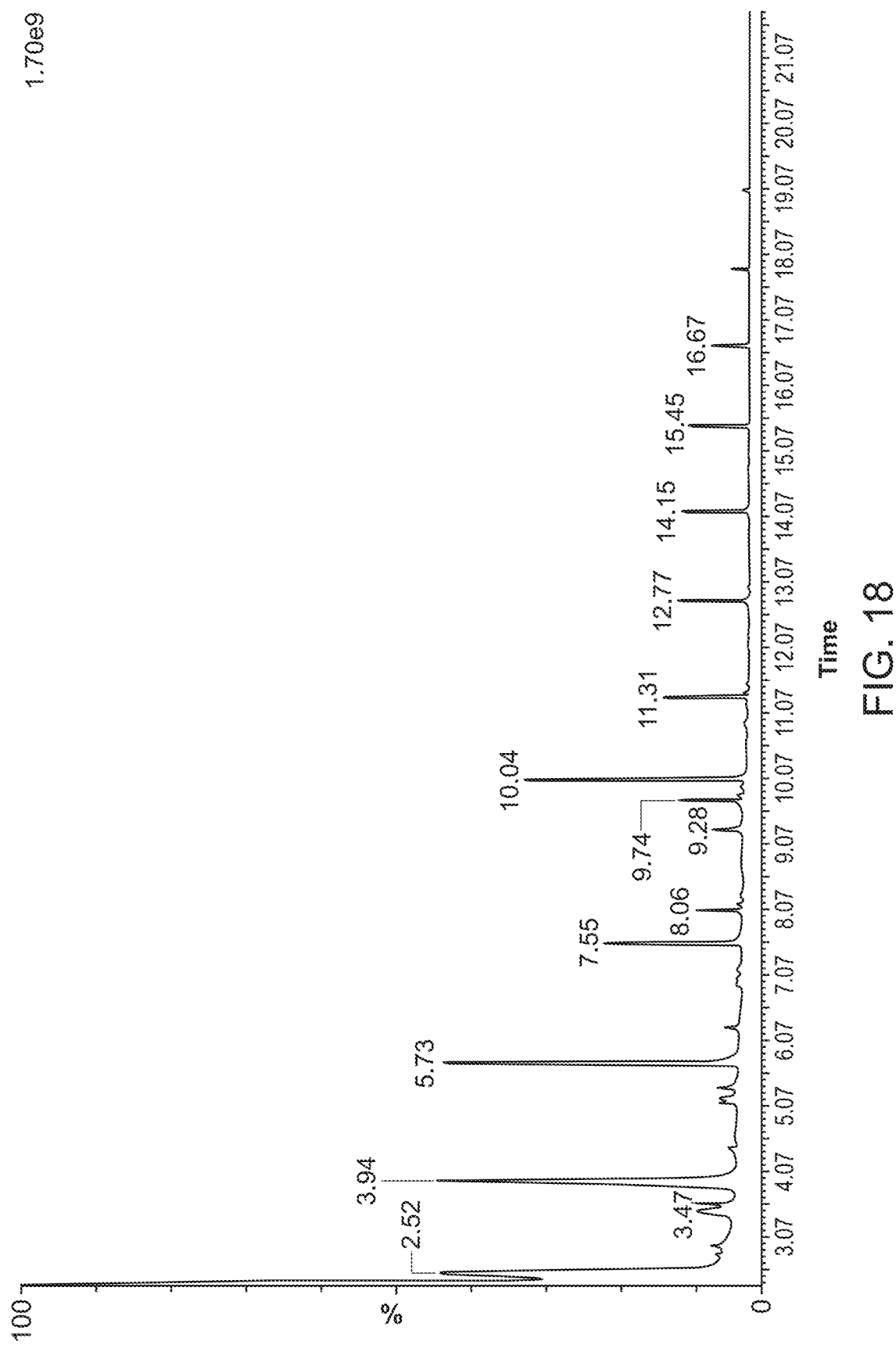

FIG. 18 shows GC-Ms analysis obtained using $CuO_{(60)}/ZnO_{(30)}/Al_2O_{3(10)}$ supported on $Al_2O_3$ catalysts at 220° C. and under 10 bar.

Figure 19:
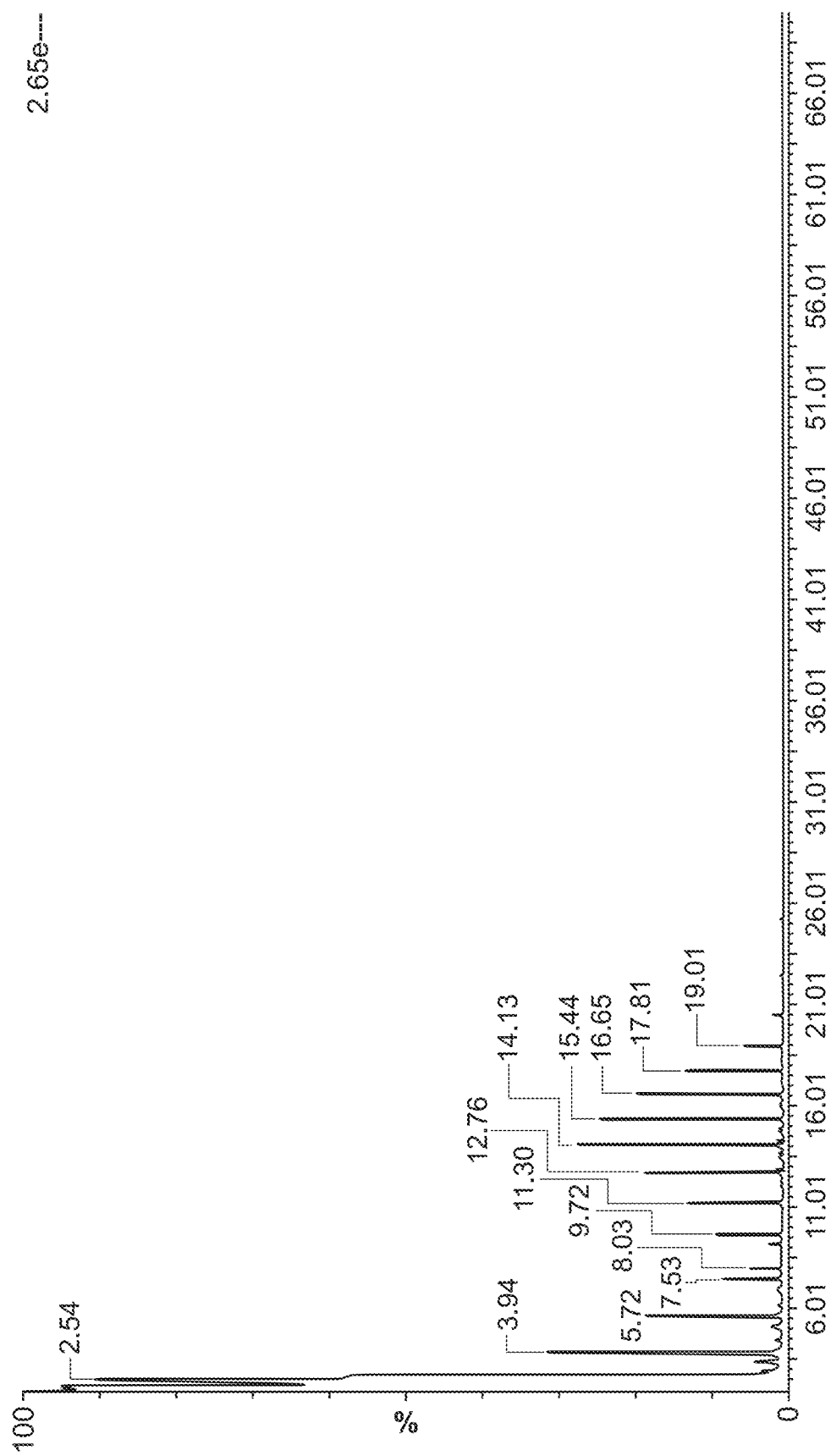

FIG. 19 shows GC-Ms analysis obtained using $CuO_{(60)}/ZnO_{(30)}/Al_2O_{3(10)}$ supported on $Al_2O_3$ catalysts at 180° C. and under 30 bar.

Figure 20:
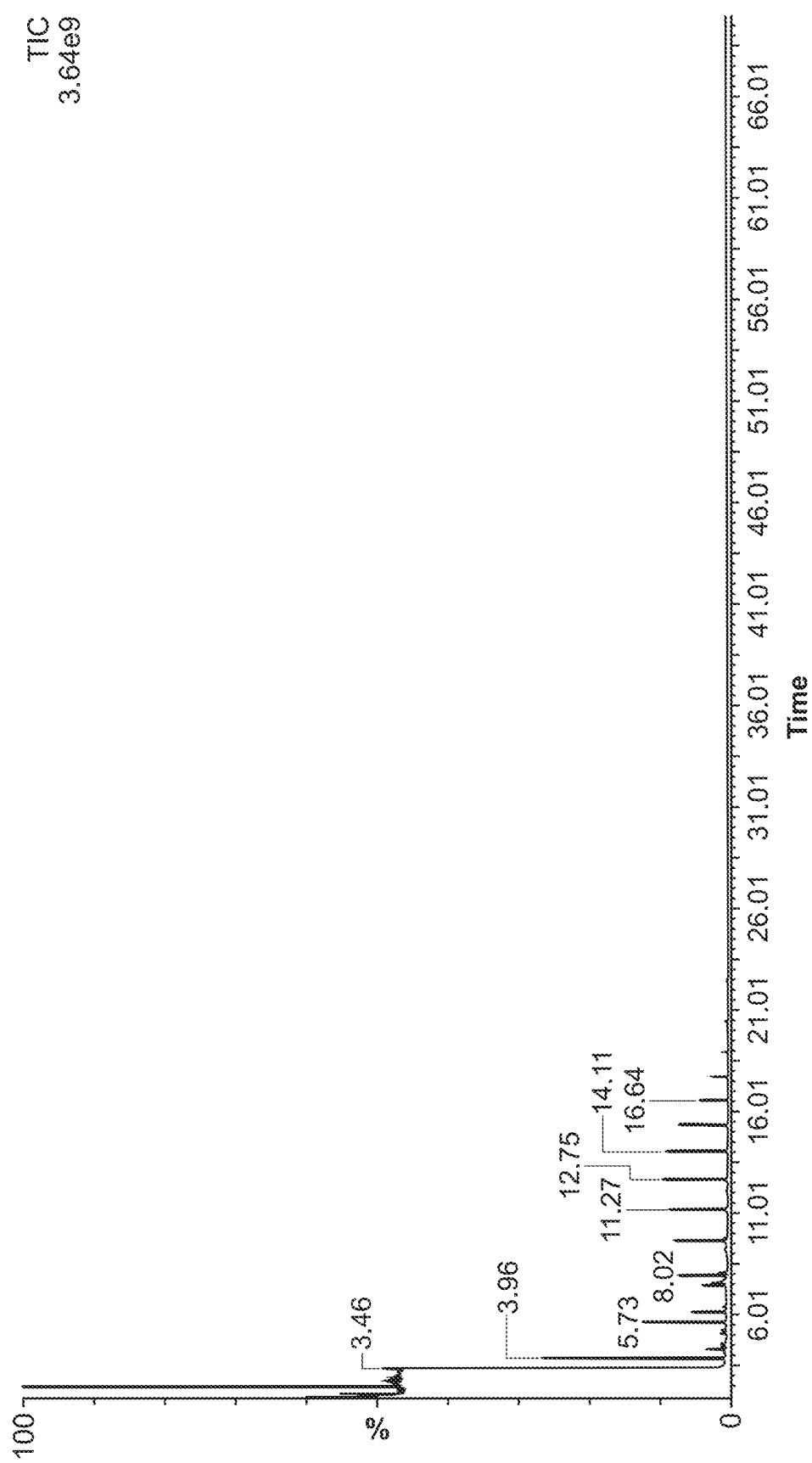

FIG. 20 shows GC-Ms analysis obtained using $CuO_{(60)}/ZnO_{(30)}/Al_2O_{3(10)}$ supported on $Al_2O_3$ catalysts at 250° C. and under 20 bar.

Figure 21:
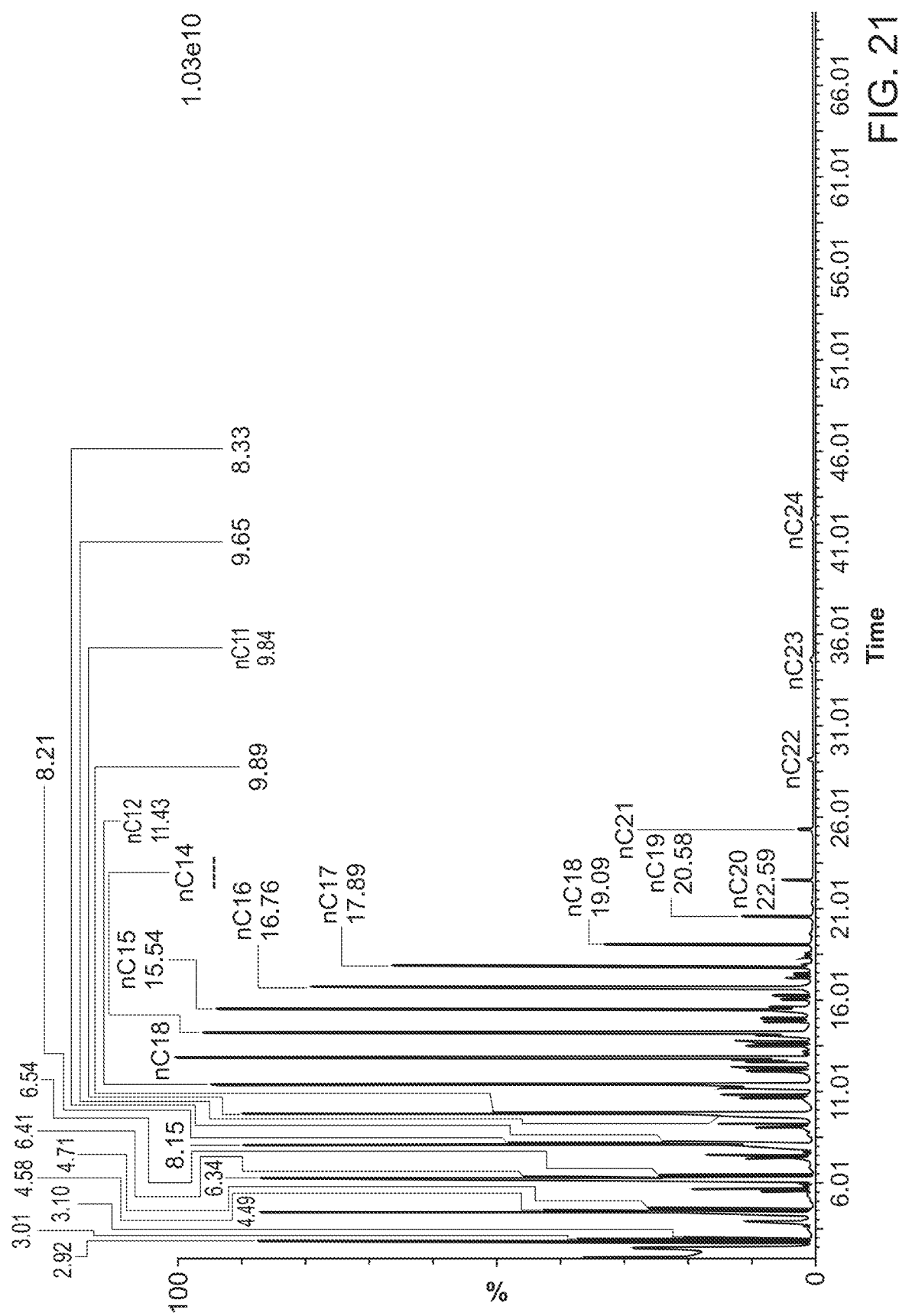

FIG. 21 shows GC-Ms analysis obtained using $CuO_{(75)}/ZnO_{(15)}/Al_2O_{3(10)}$ supported on $Al_2O_3$ catalysts at 250° C. and under 20 bar.

DETAILED DESCRIPTION

As used herein, "syngas," refers to a fuel mixture that comprises hydrogen ($H_2$), carbon monoxide (CO), and optionally carbon dioxide ($CO_2$).

Set forth herein is a facile-one pot approach for the controlled fabrication of Cu/Zn mixed oxides in situ supported on $Al_2O_3$ via the combustion of metal precursors with the assistance of glycine followed by thermal annealing under air. The resulting catalysts were used for the thermal conversion of syngas to heavy hydrocarbons in tubular fixed bed reactors—mimicking the Fischer-Tropsch synthesis.

Set forth herein is a simple, facile, one-pot process, which does not rely on special laboratory equipment or technique; just oven and hot stirrer are needed.

The processes set forth herein result in high mass production of the significant catalysts. The processes set forth herein can be easily extended for the synthesis of other metal-oxide catalysts with and without supports by varying the metals precursors used as reactants.

The catalysts set forth herein are in situ supported without the need for additional steps. This means that, in some examples, the CuO and ZnO nanoparticles are supported on an $Al_2O_3$ support in one-step, with an additional step being used for making the $Al_2O_3$-support. This not only allowed the homogenous mixing of metal precursors at the atomic level, instead of their segregation over the support, but it also enhanced the electronic interaction between metals and support.

The catalysts set forth herein include the electronic and catalytic properties of metal-oxides and supported catalysts since they are composed of Cu-oxide with Zn-oxide in situ-supported on $Al_2O_3$.

The synergism between ZnO and CuO facilitates the high adsorption of syngas over the catalysts under low pressure, while their coupling with the $Al_2O_3$ support induces the hydration and subsequent reduction process resulting in the formation of wide ranges of heavy hydrocarbons.

The complete conversion of syngas to hydrocarbons was achieved within a temperature range between 180-250° C. as well as a pressure range between 10-50 bar and as a function of the ratio between $CuO/ZnO/Al_2O_3$ of (40/30/30, 60/30/10, and 75/15/10, respectively) via the combusting of Cu/Zn/Al metal precursors, glycine and water to form a powder followed by annealing of that powder. It was observed that CuO/ZnO support-free, prepared by combusting Cu/Zn metal precursors, glycine and water to form a powder, followed by annealing of that powder, can also produce the same hydrocarbon fuel products but with less yield (10% lower) than the corresponding material when supported on $Al_2O_3$).

The reaction products (100% yield) were a series of liquid hydrocarbons of $nC_4$-$nC_{24}$ each composed of iso-paraffin, olefins, and aromatic at 10-50 bar at 250° C. using $CuO_{(75)}/ZnO_{(15)}/Al_2O_{3(10)}$, $CuO_{(60)}/ZnO_{(30)}/Al_2O_{3(10)}$, and $CuO_{(40)}/ZnO_{(30)}/Al_2O_{3(30)}$ catalysts (FIG. 8 to FIG. 21). At higher pressure of 70 bar, a series of heavy alcohols $nC_1$-$nC_9$ including methanol, ethanol, propanol, butanol, pentanol, hexanol, heptanol, and octanol were produced (FIG. 17) using $CuO_{(75)}/ZnO_{(15)}/Al_2O_{3(10)}$ catalyst at 250° C. as well.

The catalysts set forth herein are superior to all previous reported metal-based, carbon-based catalysts under the same reaction conditions or parameters at 180-250° C. under 10-30 bar (Table 1) as well as the type of the products.

The catalysts set forth herein possess a variety of advantages and benefits including, but not limited to, the following.

The fabrication process set forth herein is a simple one-pot approach without the need for multiple reaction steps or hazardous chemicals. The composition of the catalysts set forth herein can be tuned and modified with respect to their metal/metal oxide ratios, and/or support type including Cu/Zn with ratios of 5/1, 2/1, and 1.3/1 and Cu/Al ratio of 7.5/1, 6/1, and 1.3/1 to form 3 main catalysts $CuO_{(75)}/ZnO_{(15)}/Al_2O_{3(10)}$, $CuO_{(60)}/ZnO_{(30)}/Al_2O_{3(10)}$, and $CuO_{(40)}/ZnO_{(30)}/Al_2O_{3(30)}$. These catalyst produced the same products, however, $CuO_{(75)}/ZnO_{(15)}/Al_2O_{3(10)}$ produced the highest yield.

The catalysts set forth herein include Cu/Zn oxides and Al-oxide which include the elements Cu, Zn, and Al which are all abundant, inexpensive and accessible raw materials The is the first disclosure of catalysts of Cu oxide/Zn oxide supported on Al-oxide or zeolite for use in Fischer-Tropsch reactions to produce liquid hydrocarbons and/or alcohols in a fixed bed reactor. The catalysts and processes herein can work under any feeding rate of syngas (e.g. $H_2$/CO with a feeding rate ratios of 2/0.5), to produce the same finger print of Fischer-Tropsch products with high yield.

In some examples, the processes herein produce products including alcohols of methanol to butanol and liquid hydrocarbon fuels from $C_5$ to $C_{25}$ each composed of iso-paraffin, olefins, and aromatic on $CuO_{(75)}/ZnO_{(15)}/Al_2O_{3(10)}$, $CuO_{(60)}/ZnO_{(30)}/Al_2O_{3(10)}$, and $CuO_{(40)}/ZnO_{(30)}/Al_2O_{3(30)}$ catalysts under 10-50 bar at 180-250° C. (FIG. 8 to FIG. 21). Meanwhile raising the pressure to 70 bar at 250° C. produced liquid hydrocarbons $C_5$ to $C_{25}$, e.g., iso-paraffin, olefins, and aromatic but also with series of heavy alcohols from methanol to octanol with their isomers using $CuO_{(75)}/ZnO_{(15)}/Al_2O_{3(10)}$ catalyst at 70 bar (FIG. 17). In some examples, these reaction products can be obtained at ambient reaction conditions including pressures from 10 to 40 bar, temperatures from 180-250° C. In some examples, the liquid hydrocarbon fuels from $C_5$ to $C_{25}$ are groups of mixed products but all contain the same carbon number.

In some examples, increasing the molar ratio 5/1 and 2/1 of Cu-oxide to Zn-oxide that used to form catalyst $CuO_{(75)}/ZnO_{(15)}/Al_2O_{3(10)}$ enhances the production yield significantly up to $C_{25}$.

In some examples, using Al-oxide or ZSM-5 as supports enhances the yield of heavy hydrocarbons.

Figure 12:
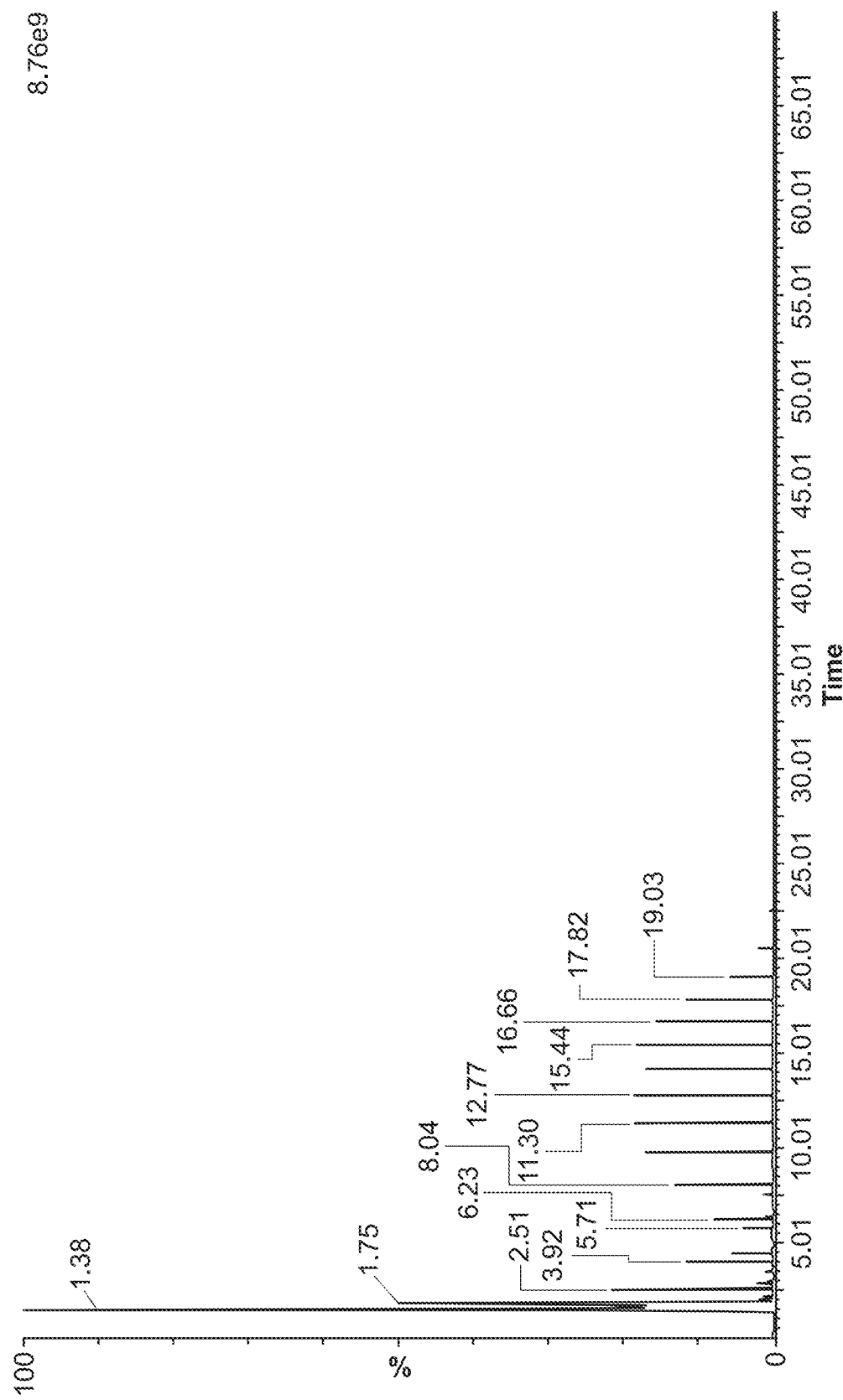
FIG. 12 shows GC-Ms analysis carried out for the liquid products obtained using freestanding $CuO_{(60)}/ZnO_{(30)}$ catalysts at 250° C. and under 40 bar.
Figure 13:
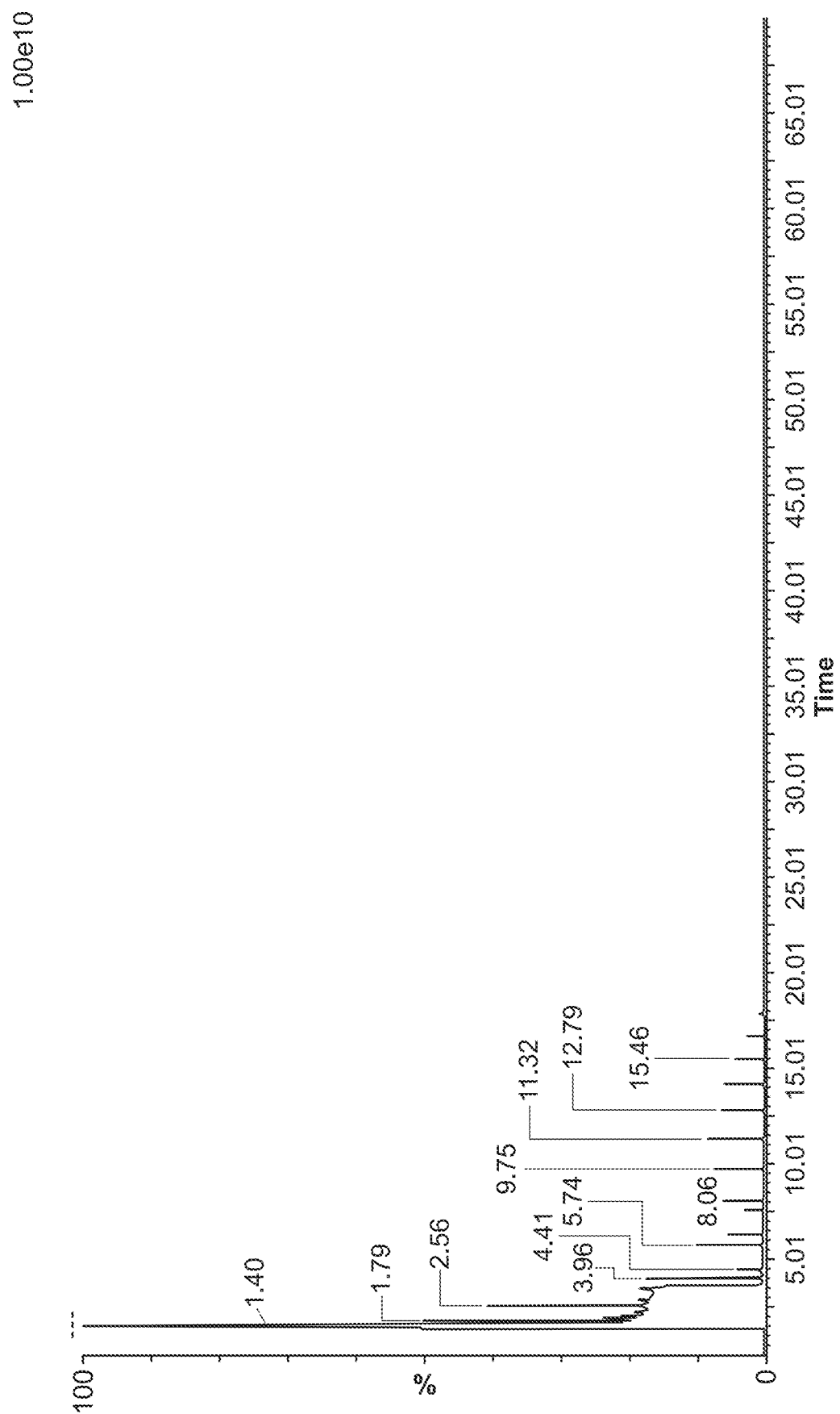
FIG. 13 shows GC-Ms analysis carried out for the liquid products obtained using freestanding $CuO_{(60)}/ZnO_{(30)}/Al_2O_{3(10)}$ supported on $Al_2O_3$ catalysts at 250° C. and under 40 bar.
Figure 14:
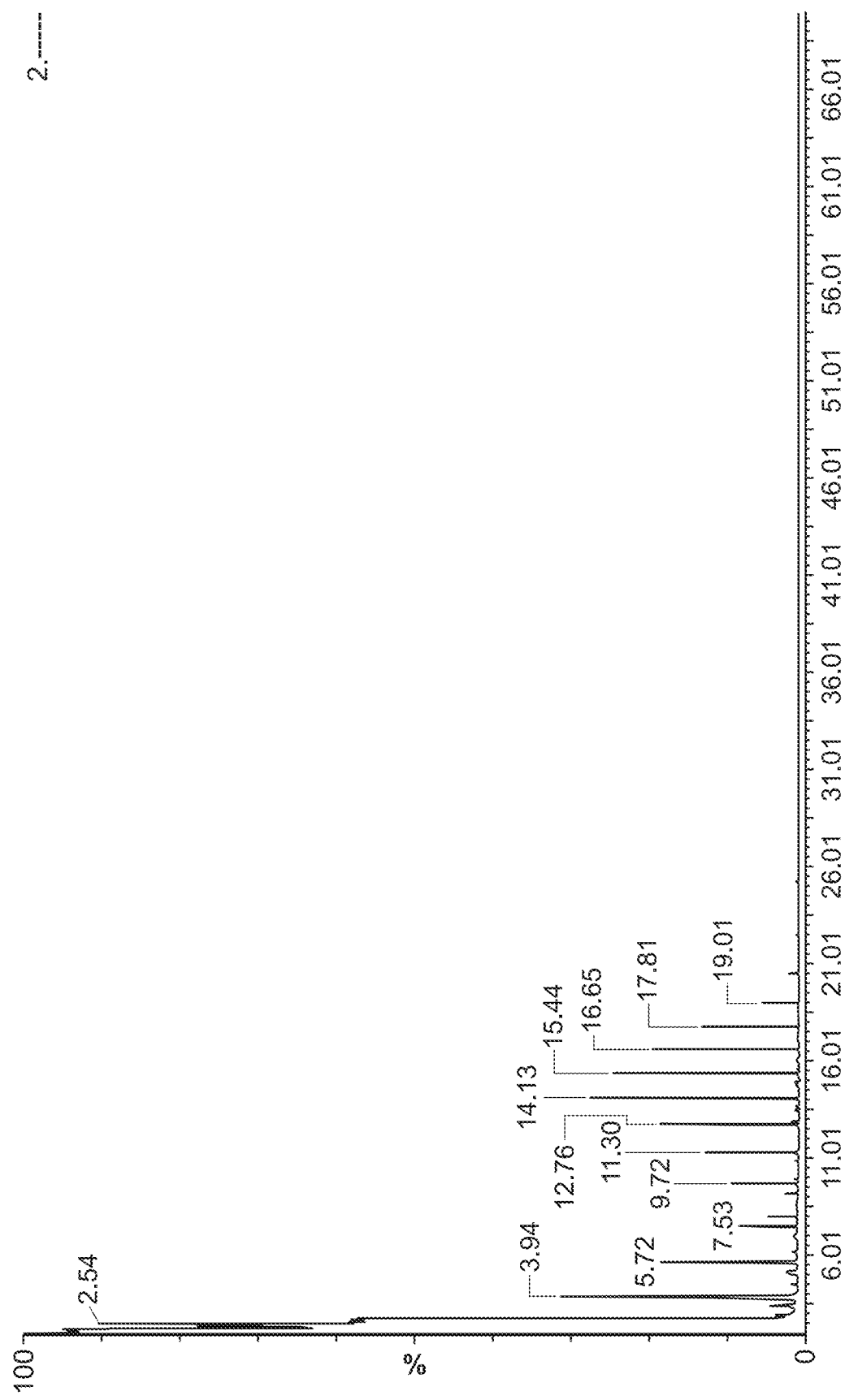
FIG. 14 shows GC-Ms analysis carried out for the liquid products obtained using $CuO_{(60)}/ZnO_{(30)}/Al_2O_{3(10)}$ supported on $Al_2O_3$ catalysts at 25 0° C. and under 40 bar.
Figure 15:
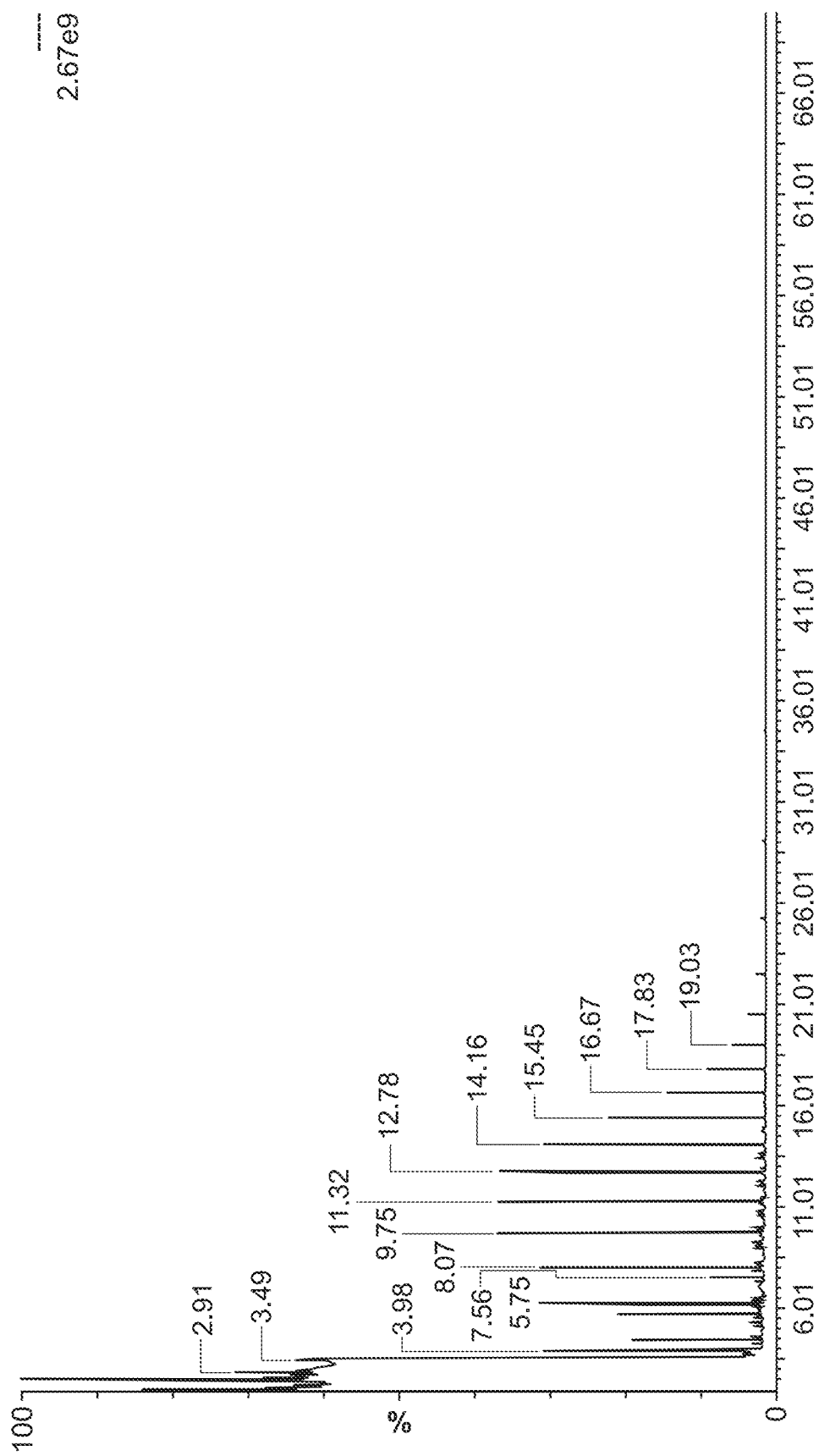
FIG. 15 shows GC-Ms analysis carried out for the liquid products obtained using $CuO_{(60)}/ZnO_{(30)}/Al_2O_{3(10)}$ supported on $Al_2O_3$ catalysts at 250° C. and under 30 bar.
Figure 16:
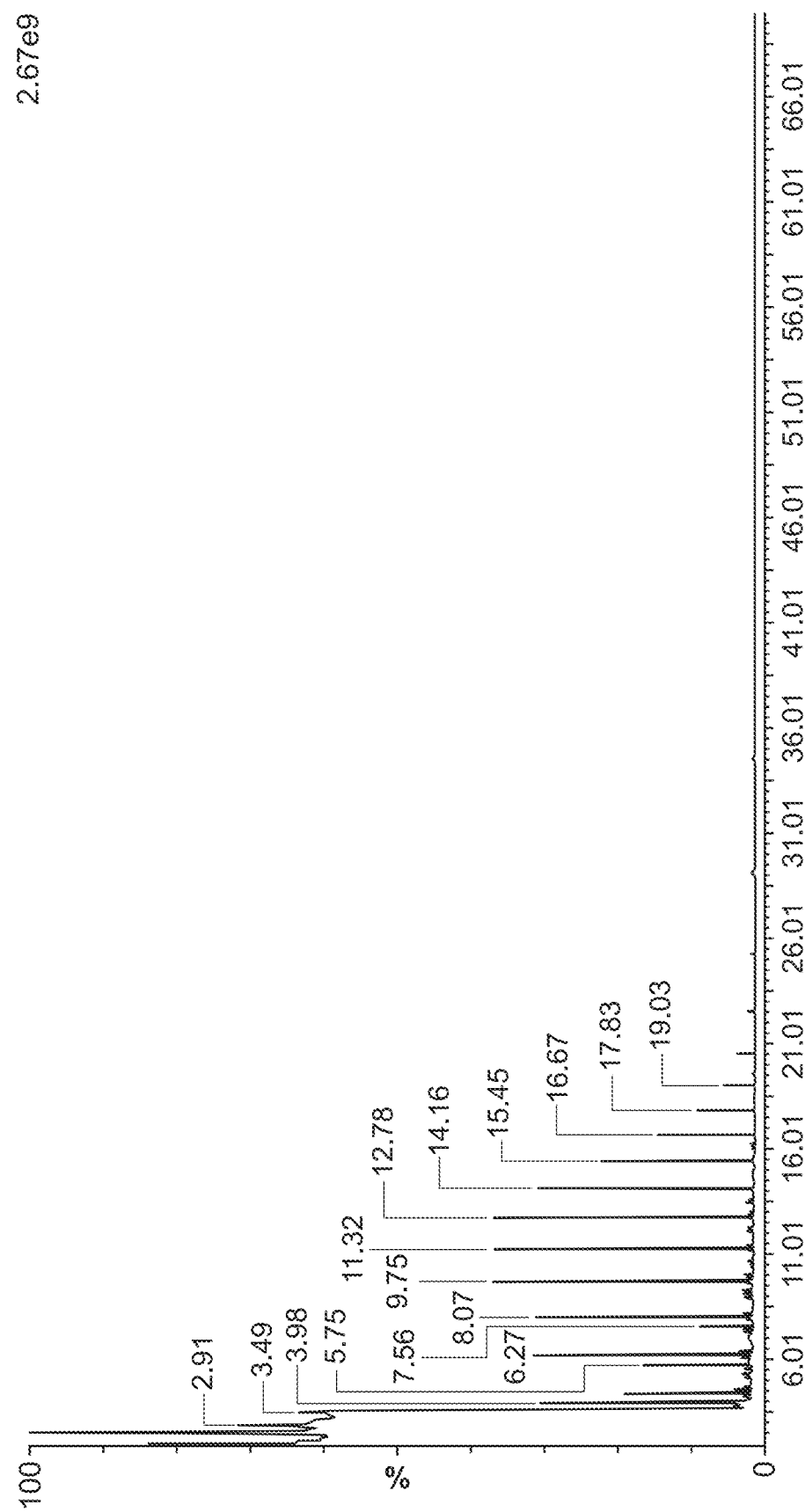
FIG. 16 shows GC-Ms analysis carried out for the liquid products obtained using $CuO_{(75)}/ZnO_{(15)}/Al_2O_{3(10)}$ supported on $Al_2O_3$ catalysts at 250° C. and under 30 bar.
Figure 17A:
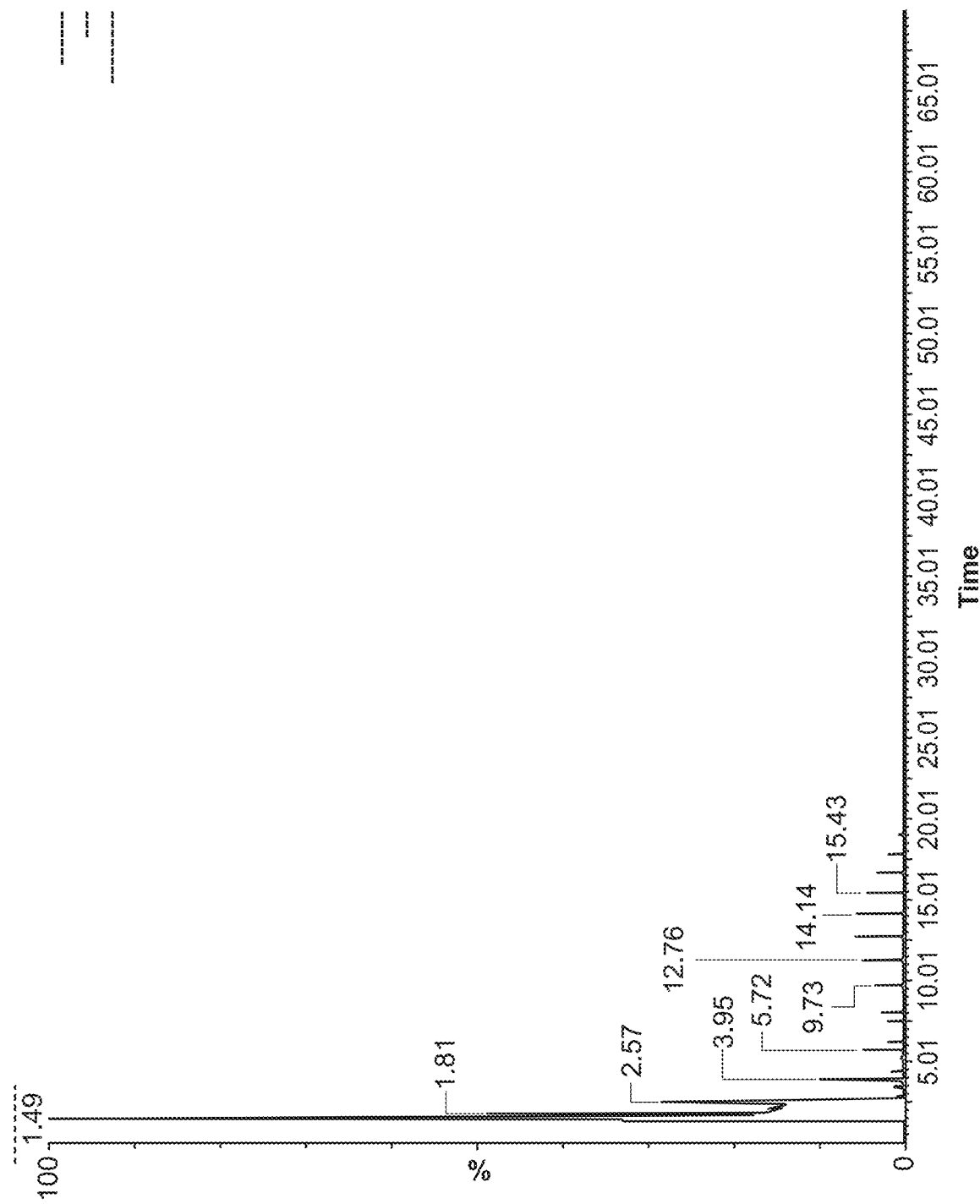
Figure 17B:
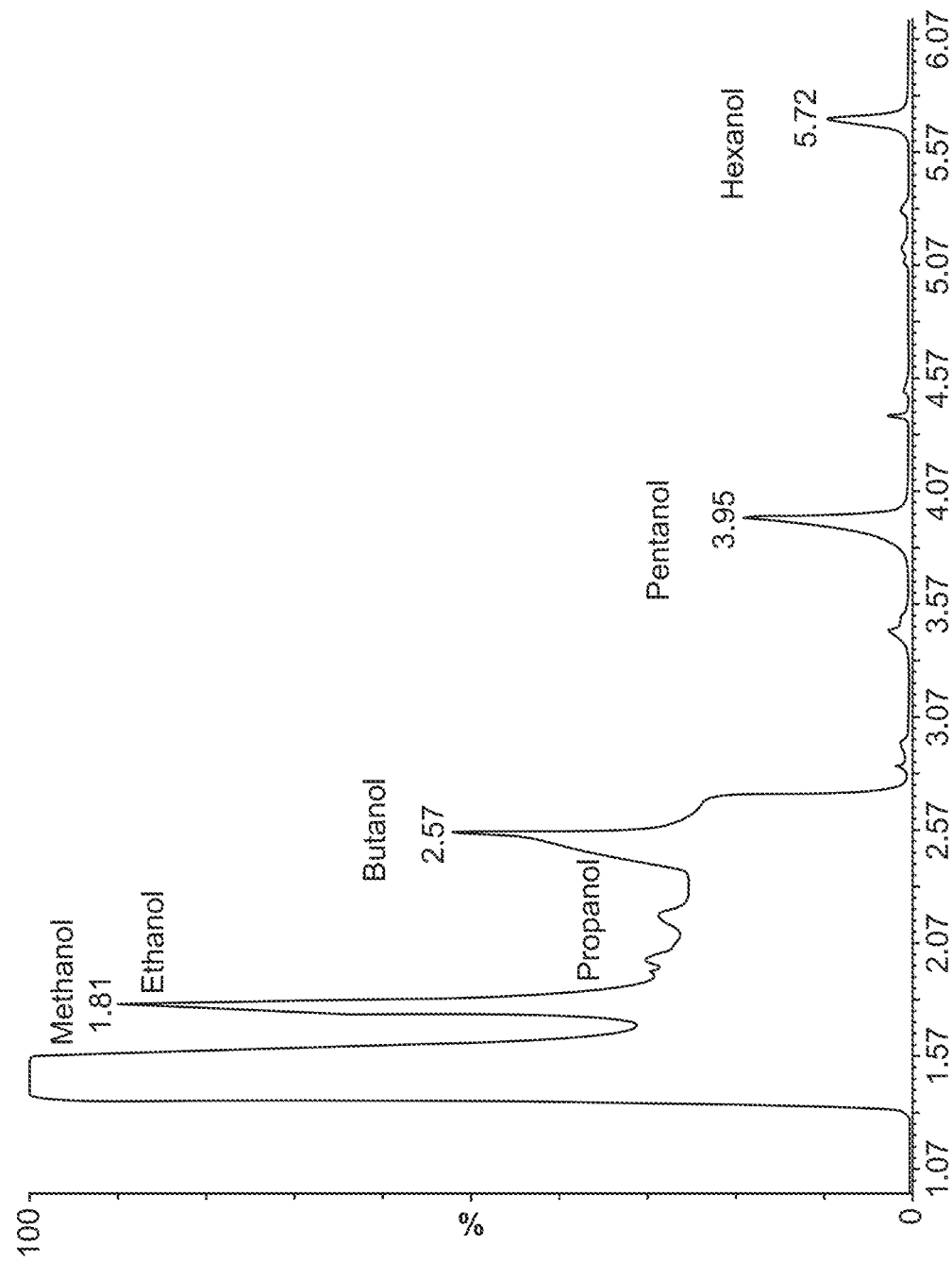
Figure 17C:
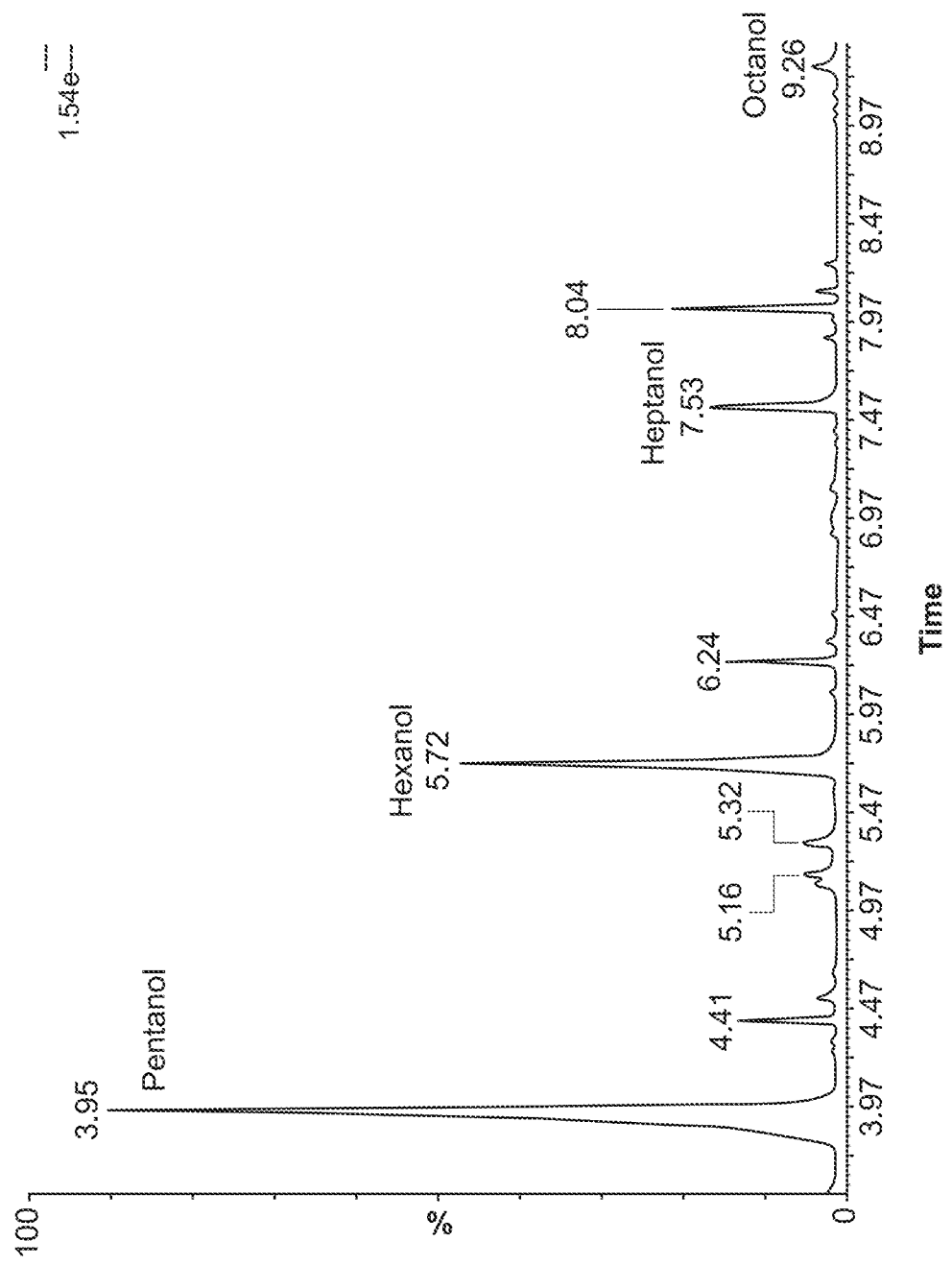
Figure 17D:
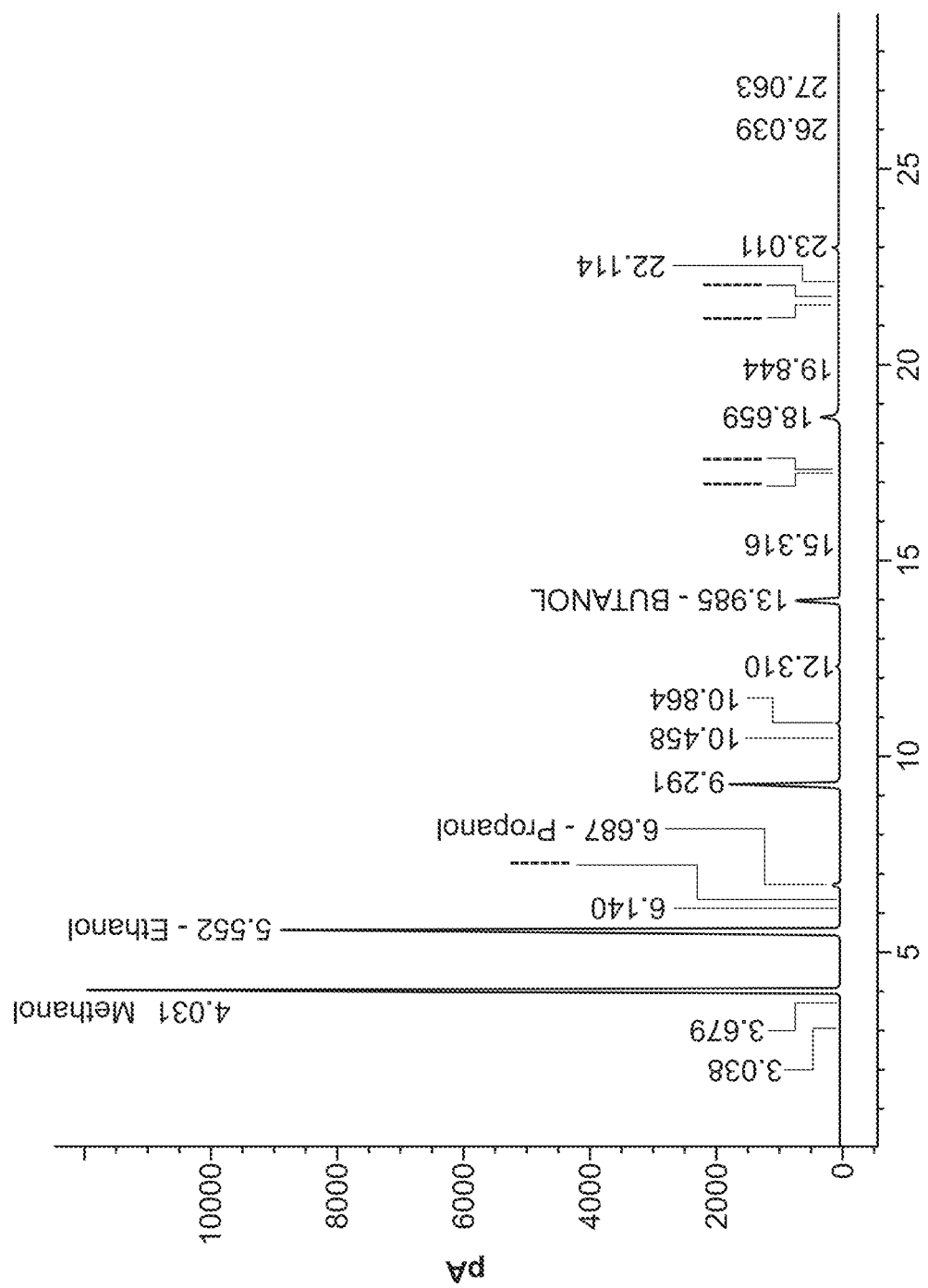

In some examples, the catalytic system including freestanding $CuO_{(60)}/ZnO_{(30)}$ without $Al_2O_3$— or ZSM-5 supports can produce the same hydrocarbon (FIG. 12).

In some examples, the yield of alcohols from the processes set forth here, increase with increasing reaction pressure.

In some examples, the molar ratio 5/1 and 2/1 of Cu-oxide to Zn-oxide enhances the production yield significantly.

The processes set forth herein are not limited. The processes can increase the production rate of formation of Fischer-Tropsch products at ambient conditions.

Compositions

In some examples, set forth herein is a composition comprising CuO and ZnO on $Al_2O_3$, wherein the composition comprises:

35 to 80 percent by mole CuO;

25 to 35 percent by mole ZnO; and 5 to 15 percent by mole $Al_2O_3$;

wherein the total percent by mole amount of Cu, ZnO, and $Al_2O_3$ is 100.

In some examples, including any of the foregoing, the composition is on a support selected from aluminum oxide, zeolite, a metal oxide, carbon, a carbon-based support, graphene, graphene-based support, metal organic framework support, and combinations thereof. In some examples, the support is aluminum oxide. In some examples, the support is zeolite. In some examples, the support is a metal oxide. In some examples, the support is carbon. In some examples, the support is a carbon-based support. In some examples, the support is graphene. In some examples, the support is graphene-based support. In some examples, the support is metal organic framework support.

In some examples, including any of the foregoing, the comprises:
40 percent by mole CuO;
30 percent by mole ZnO; and
30 percent by mole $Al_2O_3$.

In some examples, including any of the foregoing, the comprises:
60 percent by mole CuO;
30 percent by mole ZnO; and
10 percent by mole $Al_2O_3$.

In some examples, including any of the foregoing, the comprises:
75 percent by mole CuO;
15 percent by mole ZnO; and
10 percent by mole $Al_2O_3$.

In some examples, set forth herein is a composition comprising CuO and ZnO on $Al_2O_3$, wherein the composition comprises: CuO, ZnO, and $Al_2O_3$. In some examples, including any of the foregoing, the CuO is present at 35 to 80 percent by mole CuO. In some examples, including any of the foregoing, the ZnO is present at 25 to 35 percent by mole ZnO. In some examples, including any of the foregoing, the $Al_2O_3$ is present at 5 to 15 percent by mole $Al_2O_3$. In some examples, including any of the foregoing, the CuO is present at 35, 40, 45, 50, 55, 60, 65, 70, 75, or 80 percent by mole. In some examples, including any of the foregoing, the ZnO is present at 25, 30, or 35 percent by mole. In some examples, including any of the foregoing, the $Al_2O_3$ is present at 5, 10, or 15 percent by mole. In these examples, the total percent by mole amount of Cu, ZnO, and $Al_2O_3$ is 100. In some examples, including any of the foregoing, the CuO is present at 35 percent by mole. In some examples, including any of the foregoing, the CuO is present at 40 percent by mole. In some examples, including any of the foregoing, the CuO is present at 45 percent by mole. In some examples, including any of the foregoing, the CuO is present at 50 percent by mole. In some examples, including any of the foregoing, the CuO is present at 55 percent by mole. In some examples, including any of the foregoing, the CuO is present at 60 percent by mole. In some examples, including any of the foregoing, the CuO is present at 65 percent by mole. In some examples, including any of the foregoing, the CuO is present at 70 percent by mole. In some examples, including any of the foregoing, the CuO is present at 75 percent by mole. In some examples, including any of the foregoing, the CuO is present at 80 percent by mole. In some examples, including any of the foregoing, the ZnO is present at 25 percent by mole. In some examples, including any of the foregoing, the ZnO is present at 30 percent by mole. In some examples, including any of the foregoing, the ZnO is present at 35 percent by mole. In some examples, including any of the foregoing, the $Al_2O_3$ is present at 5 percent by mole. In some examples, including any of the foregoing, the $Al_2O_3$ is present at 10 percent by mole. In some examples, including any of the foregoing, the $Al_2O_3$ is present at 15 percent by mole.

In some examples, including any of the foregoing, the catalyst is characterized by spherical-like nanoparticles.

In some examples, including any of the foregoing, the spherical-like nanoparticles have an average diameter of 30 nm.

In some examples, including any of the foregoing, the catalyst is characterized by amorphous aggregated oxide particles.

In some examples, including any of the foregoing, the amorphous aggregated oxide particles have an average diameter of 400-800 nm.

In some examples, including any of the foregoing, the catalyst is exclusive of any impurities as determined by x-ray photo-electron spectroscopy. For example, FIG. 5 shows the formation of the catalysts without any impurities.

In some examples, including any of the foregoing, the elements Cu, Zn, and Al are evenly distributed in the catalyst.

In some examples, including any of the foregoing, the atomic content of Cu, Zn, Al, O, and N is 8.68, 5.05, 18.86, and 63.77, and 3.65, respectively.

In some examples, including any of the foregoing, the atomic content of Cu, Zn, Al, O, and N is 13.62, 9.09, 11.47, 62.95, and 2.89, respectively In some examples, set forth herein is a process for making CuO/ZnO supported on $Al_2O_3$ comprising:
a. combusting metal precursors, glycine and water to form a powder; and
b. annealing the powder;
c. wherein the metal precursors are selected from the group consisting of $Cu(NO_3)_2$, $Zn(NO_3)_2$, and $Al(NO_3)_2$.

In some examples, including any of the foregoing, the combusting occurs at 420° C. until dry and ignition.

In some examples, the metal precursors are selected from the group consisting of $Cu(NO_3)_2$ or $Cu(OH)_2$, $Zn(NO_3)_2$ or ZnO, and $Al(NO_3)_2$ or $Al(OH)_3$.

In some examples, including any of the foregoing, the annealing occurs at 600° C.

Processes

In some examples, set forth herein is a process for converting syngas into usable liquid hydrocarbons and alcohols comprising contacting syngas to a catalyst set forth herein under syngas reaction conditions. Herein, the feeding rate ratio may also be a molar ratio unless specified to the contrary.

In some examples, set forth herein is a process for converting syngas into usable liquid $nC_4$-$nC_{24}$ hydrocarbons and $nC_1$-$nC_9$ alcohols comprising contacting syngas to a catalyst set forth herein under syngas reaction conditions including $H_2$/CO syngas with a feeding rate ratio of 2/0.5, at 180-250° C. under pressure of 10-70 bar. Herein, the feeding rate ratio is also a molar ratio unless specified to the contrary.

In some examples, including any of the foregoing, the contacting occurs between 25° C. to 300° C.

In some examples, including any of the foregoing, the contacting occurs between 1 bar to 100 bar.

In some examples, including any of the foregoing, during the contacting the CO/$H_2$ feeding rate ratio of 0.05/2, respectively. In some examples, the feeding ratio is from 0.05 to 2, 1 to 3, to 2, or 1 to 1.

In some examples, including any of the foregoing, the process produces liquid hydrocarbons. In some examples, the the process produces liquid hydrocarbons at pressures greater than 50 bar and at a temperature greater than 200° C. using $CuO_{(40)}/ZnO_{(30)}/Al_2O_{3(30)}$, $CuO_{(60)}/ZnO_{(30)}/Al_2O_{3(10)}$, and $CuO_{(75)}/ZnO_{(15)}/Al_2O_{3(10)}$ catalysts.

In some examples, including any of the foregoing, the process produces liquid alcohols. Each of the catalysts set forth herein may produce the same products. However, the $CuO_{(60)}/ZnO_{(30)}/Al_2O_{3(10)}$ catalyst produces a higher liquid yield by volume of those products.

In some examples, including any of the foregoing, the process produces a combination of liquid hydrocarbons and alcohols.

In some examples, including any of the foregoing, the process produces a combination of liquid hydrocarbons and alcohols using $CuO_{(40)}/ZnO_{(30)}/Al_2O_{3(30)}$, $CuO_{(60)}/ZnO_{(30)}/Al_2O_{3(10)}$, and $CuO_{(75)}/ZnO_{(15)}/Al_2O_{3(10)}$ catalysts under pressure 10-70 bar at a temperature 150-250° C. In some examples, the pressure is 10 bar. In some examples, the pressure is 10 bar. In some examples, the pressure is 20 bar. In some examples, the pressure is 30 bar. In some examples, the pressure is 40 bar. In some examples, the pressure is 50 bar. In some examples, the pressure is 60 bar. In some examples, the temperature is 150° C. In some examples, the temperature is 200° C. In some examples, the temperature is 250° C.

EXAMPLES

The following chemicals were purchased commercially unless stated otherwise. Aluminum nitrate nonahydrate, $Al(NO_3)_3.9H_2O$, ACS reagent, ≥99% (Sigma-Aldrich Chemie GmbH (Munich, Germany)). Copper(II) nitrate trihydrate $Cu(NO_3)_2.3H_2O$, assay 99-104% (Sigma-Aldrich Chemie GmbH (Munich, Germany)). Zinc Nitrate (Hexahydrate), Reagent grade, 98% $Zn(NO_3)_2.6H_2O$ Extra Pure (Sigma-Aldrich Chemie GmbH (Munich, Germany)). Aluminum oxide ($Al_2O_3$, 99.99%) Puralox Th 100/150 (Sasol GmbH (Munich, Germany)). Glycine, ReagentPlus, ≥99% (Sigma-Aldrich Chemie GmbH (Munich, Germany)).

Materials were imaged using a scanning electron microscope (SEM, Hitachi S-4800, Hitachi, Tokyo, Japan). The X-ray photoelectron spectroscopy (XPS) spectra were measured on a Kratos Axis (Ultra DLD XPS Kratos, Manchester, UK) equipped with a monochromatic Al Kα radiation source (1486.6 eV) under a UHV environment (ca. $5\times10^{-9}$ Torr). The x-ray diffraction patterns (XRD) were measured on an x-ray diffractometer (X'Pert-Pro MPD, PANalytical Co., Almelo, Netherlands) using Cu Kα X-ray source ($\lambda=1.540598$ Å). The nitrogen physisorption isotherms were measured on a Quanta chrome Instrument Corporation Autosorb-1 analyser (Quanta chrome Instrument Corporation, Boynton Beach, Fla., USA).

Example 1

Preparation of Catalysts: $CuO/ZnO/Al_2O_3$.

The combustion method was combined with thermal pyrolysis to prepare $CuO/ZnO/Al_2O_3$. Particularly, $Cu(NO_3)_2$ (2.4 g), $Zn(NO_3)_2$ (2.1 g), $Al(NO_3)_2$ (4.4 g), and glycine were mixed together in an aqueous solution of 100 mL water and then combusted at 420° C. until dry and ignition. Following that, the obtained powder was annealed under air at 600° C. (1°/min for 3 hours under air. After cooling to the room temperature, the obtained catalyst was collected and kept for further characterizations. The obtained catalysts is denoted as $CuO_{(40)}/ZnO_{(30)}/Al_2O_{3(30)}$. A second batch was prepared having ratios between Cu and Zn of $CuO_{(60)}/ZnO_{(30)}/Al_2O_{3(10)}$ and $CuO_{(75)}/ZnO_{(15)}/Al_2O_{3(10)}$.

Characterization: Catalytic Conversion of Syngas

The catalytic process was carried out via placing 100 mg of the as-formed catalysts in a fixed-bed reactor (model) connected to an online gas chromatography. The catalyst was initially pretreated under $H_2$ gas (20 mL/Min) gas at 300 for 2 hours. Following the cooling, the catalyst was exposed to the syngas ($CO/H_2$) with a total flow of 60 mL/min at different temperature and pressure. The liquid products were cooled after 24 hours and analyzed by the gas-chromatography mass-spectrometry (GC-MS) (PerkinElmer Calms 600S, USA) connected to a heat space (Perkin Elmer TurboMatrix 40 Trap), and the data were analyzed using the TurboMass pro and GC-FID (Agilent technologies, 7890A, USA).

Results

Figure 1A:
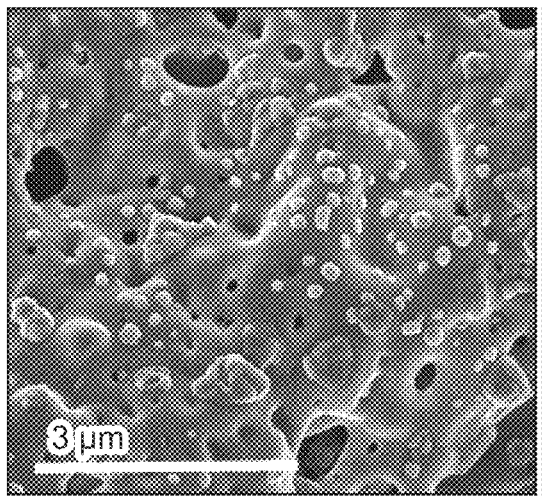
Figure 1B:
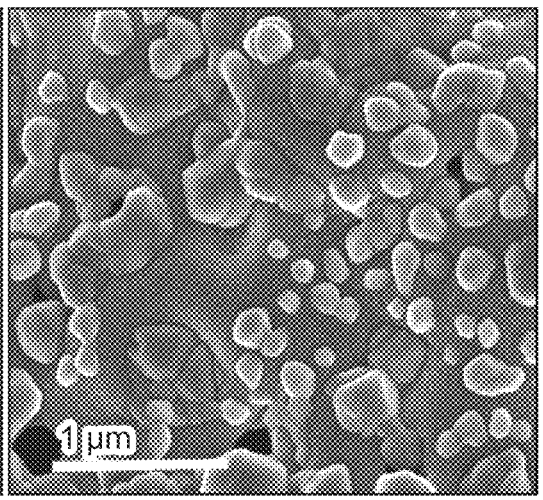
Figure 1C:
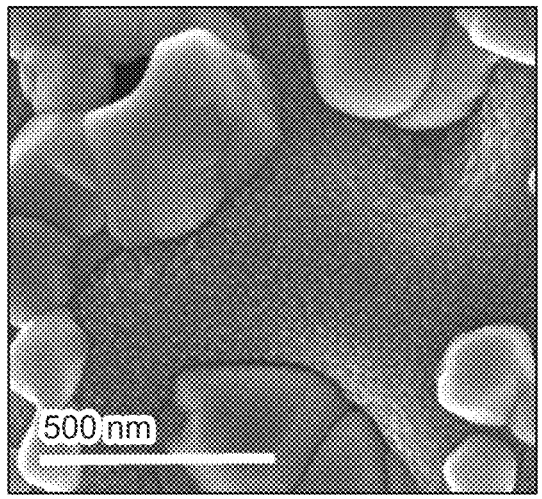

FIGS. 1a-c shows the SEM images of $CuO_{(40)}/ZnO_{(30)}/Al_2O_{3(30)}$ catalysts. The catalysts were prepared by mixing $Cu(NO_3)_2$ (2.4 g), $Zn(NO_3)_2$ (2.1 g), $Al(NO_3)_2$ (4.4 g), and glycine (4 g) together in an aqueous solution of 100 mL water and then combusting this mixture at 420° C. until dry, and ignition followed by annealing under air at 600° C. (1°/min) for 3 h under air the typical conditions. The catalyst had a mixture of spherical-like nanoparticles with an average diameter of 30 nm, well distributed with some amorphous aggregated oxide particles with an average diameter of 400-800 nm (FIGS. 1a-c). The EDX shows the coexistence of Cu, Zn, Al, and O with atomic contents of 8.68, 5.05, 18.86, 63.77, and 3.65, respectively. The EDX reveals the absence of any kind of impurities (FIG. 1d). However, the resolved N likely originated from the glycine.

Figure 2A:
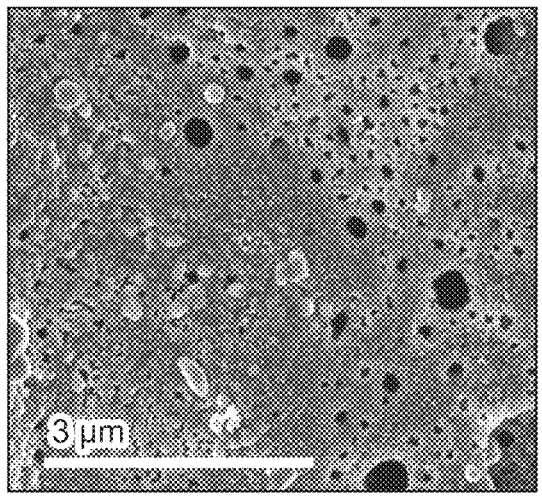
Figure 2B:
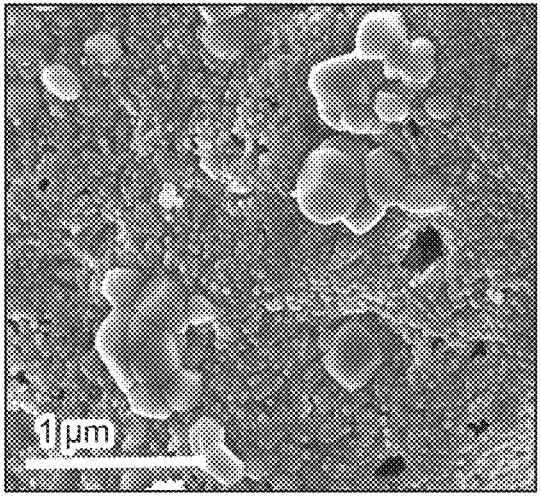
Figure 2C:
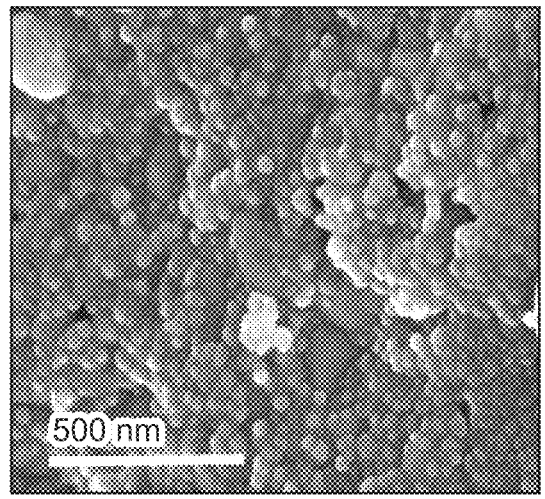

FIGS. 2a-c show SEM images of $CuO_{(60)}/ZnO_{(30)}/Al_2O_{3(10)}$. The catalysts were prepared by mixing $Cu(NO_3)_2$ (3.64 g), $Zn(NO_3)_2$ (1.82 g), $Al(NO_3)_2$ (1.472), and glycine (3.21 g) together in an aqueous solution of 100 mL water and then combusting this mixture at 420° C. until dry and ignition followed by annealed under air at 600° C. (1°/min) for 3 h under air. The catalyst formed in cluster-like assembled in network-like structure with multiple pores including meso-, micro, and macrospores (FIG. 2a). The high magnification SEM images showed the spherical-like structure of the as-formed catalysts with an average diameter of 55 nm and some aggregated particle of 300 nm (FIGS. 2b-c). The EDX showed homogenous distribution of Cu, Zn, Al, O, and N with atomic contents of 13.62, 9.09, 11.47, 62.95, and 2.89, respectively (FIG. 2d).

Figure 3A:
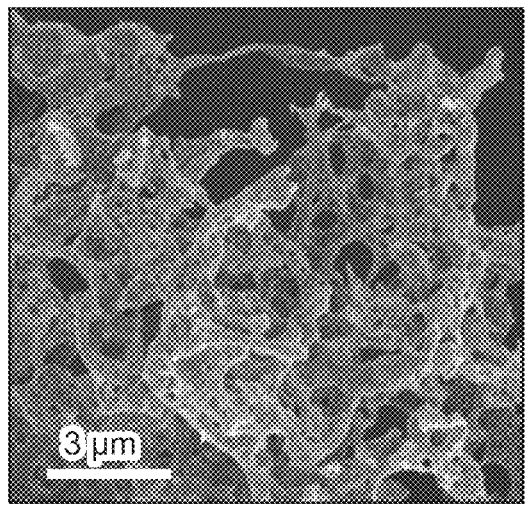
Figure 3B:
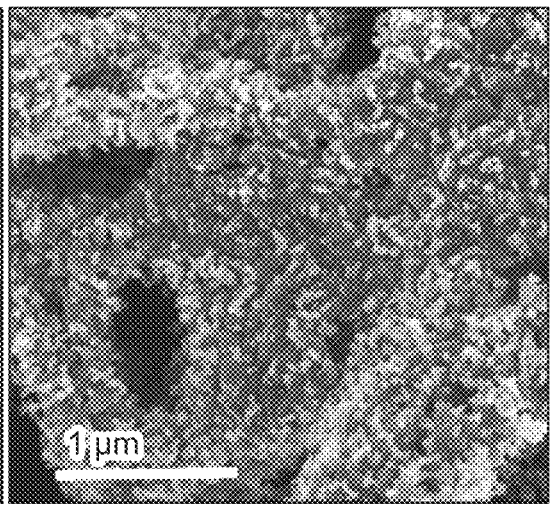
Figure 3C:
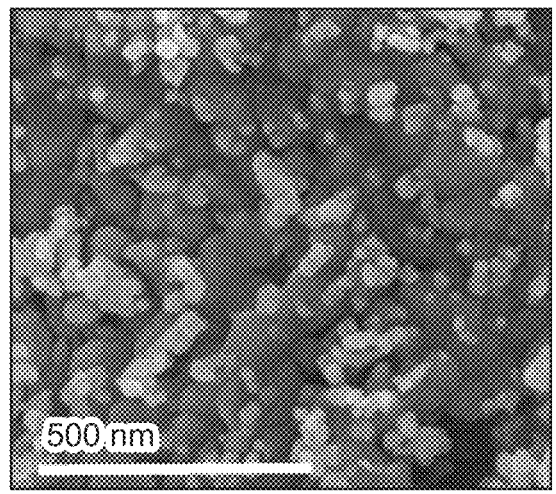

FIGS. 3a-c show SEM images of $CuO_{(75)}/ZnO_{(15)}/Al_2O_{3(10)}$. The catalysts were prepared by mixing $Cu(NO_3)_2$ (4.55 g), $Zn(NO_3)_2$ (1.09 g), $Al(NO_3)_2$ (1.472), and glycine (2.836 g) together in an aqueous solution of 100 mL water and then combusting this mixture at 420° C. until dry and ignition followed by annealed under air at 600° C. (1°/min) for 3 h under air, which led to the formation of a network of cluster-like structure in multiple porous structure including mesopores, microspores, and macrospores (FIG. 3a). The high magnification SEM images show the well distribution of semi-spherical nanoparticles (70 nm) over flakes-like structure (200-400 nm) (FIGS. 3b-c). The EDX revealed the homogenous distribution of Cu, Zn, Al, O, and N with atomic contents of 21.86, 4.44, 9.31, 61.45, and 2.94, correspondingly (FIG. 3d).

Figure 4:
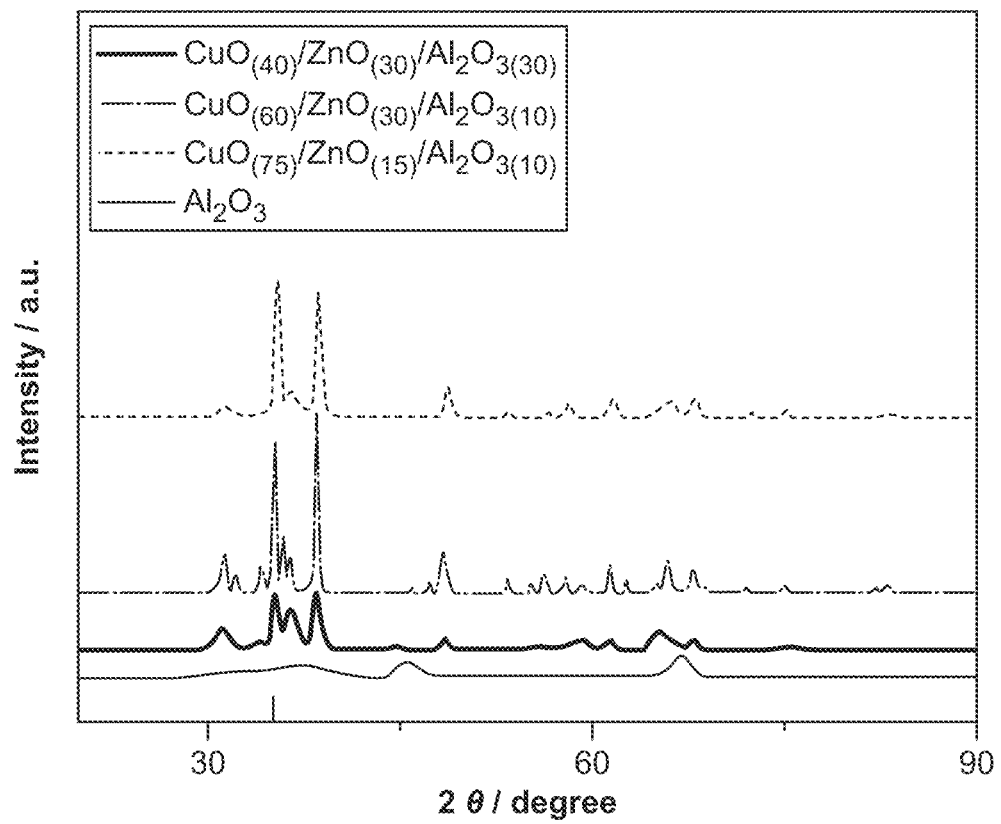

FIG. 4 shows XRD of the as-prepared catalysts using different ratios of Cu/Zn compared to pure $Al_2O_3$. The pure $Al_2O_3$ results show diffraction patterns without any impurities; meanwhile all catalysts show the typical diffraction patterns of mixed CuO and ZnO.

Figure 5A:
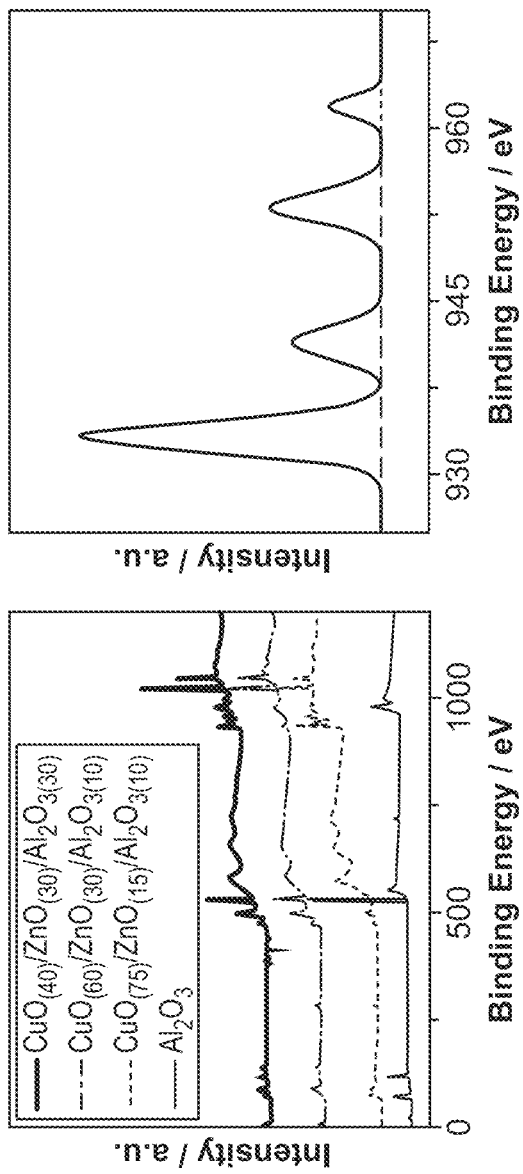
Figure 5B:
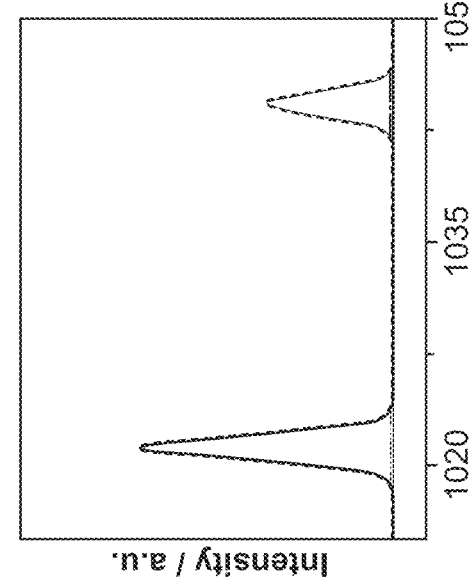
Figure 5C:
Figure 5D:

FIG. 5a shows the XPS survey of typically prepared catalysts under the same conditions, which show the core-level and the valence-bands of Cu, Zn, Al, O, and N as well as C. The composition of the as-synthesized catalysts estimated by the XPS were almost in line with the EDX. The high resolution XPS of $CuO_{(40)}/ZnO_{(30)}/Al_2O_{3(30)}$ shows the main spectra assigned to Cu2p ($2p_{3/2}$ and $2p_{1/2}$) with its corresponding 4 peaks of $Cu^0$ and $Cu^{2+}$ (FIG. 5b), Zn2p ($2p_{3/2}$ and $2p_{1/2}$) with its 2 peaks for $Zn^0$ and $Zn^{2+}$ (FIG. 5c), and O1s (FIG. 5d)).

Figure 6A:
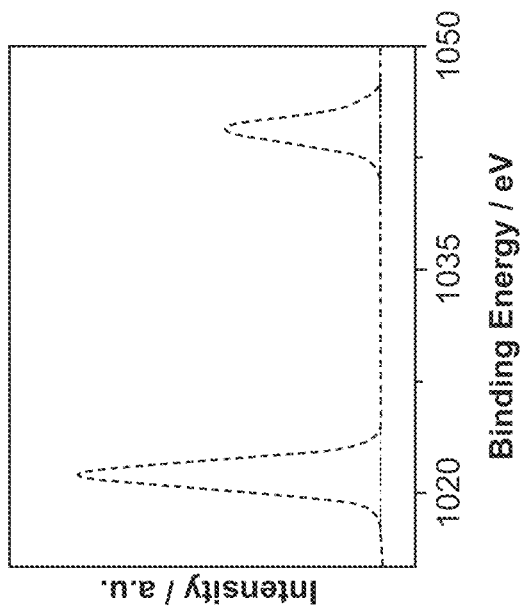
Figure 6B:
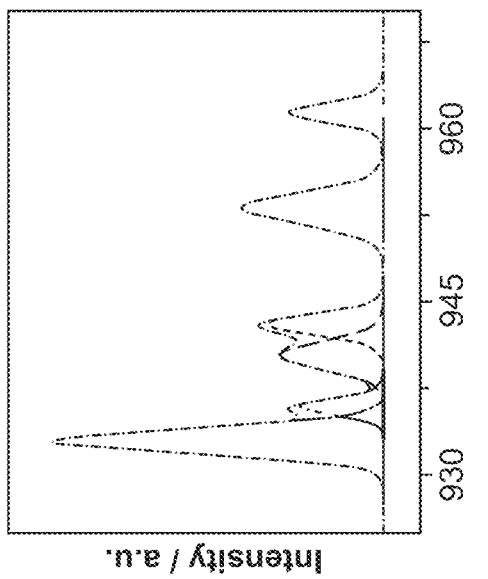
Figure 6C:
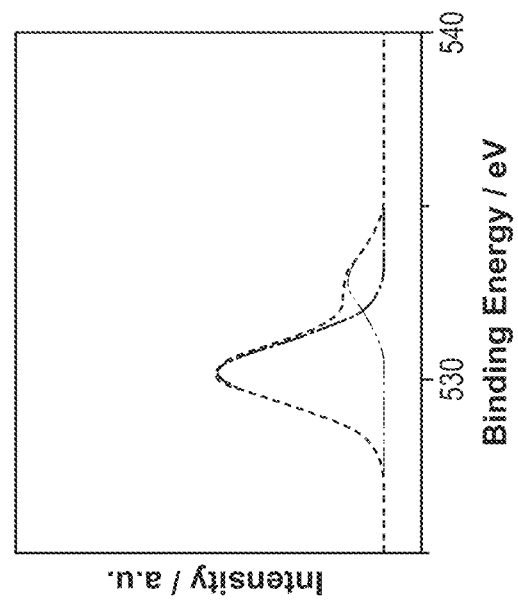

FIGS. 6a-c shows the high-resolution XPS spectra of $CuO_{(60)}/ZnO_{(30)}/Al_2O_{3(10)}$ including Cu2p ($2p_{3/2}$ and $2p_{1/2}$) with its corresponding 2 peaks of $Cu^0$ and 4 peaks of $Cu^{2+}$ (FIG. 6a), Zn2p ($2p_{3/2}$ and $2p_{1/2}$) with its 2 peaks for $Zn^0$ and $Zn^{2+}$ (FIG. 6b), and 2 peaks of O1s oxide/hydroxide (FIG. 6c). The observed higher oxidation states of Cu were attributed to its higher content in the catalysts.

Figure 7A:
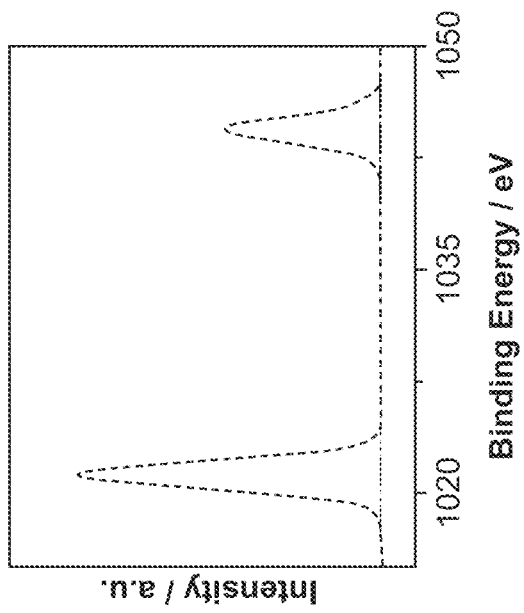
Figure 7B:
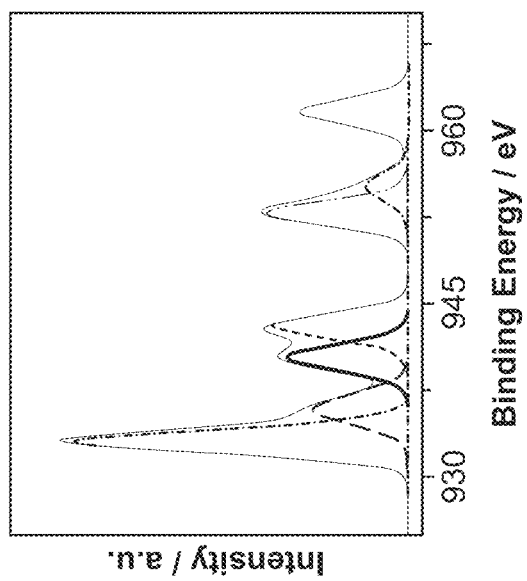
Figure 7C:
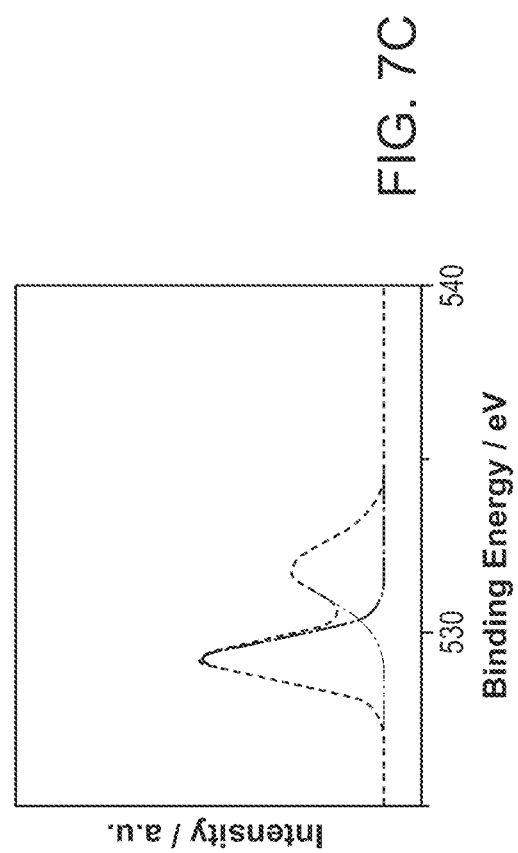
Figure 8A:
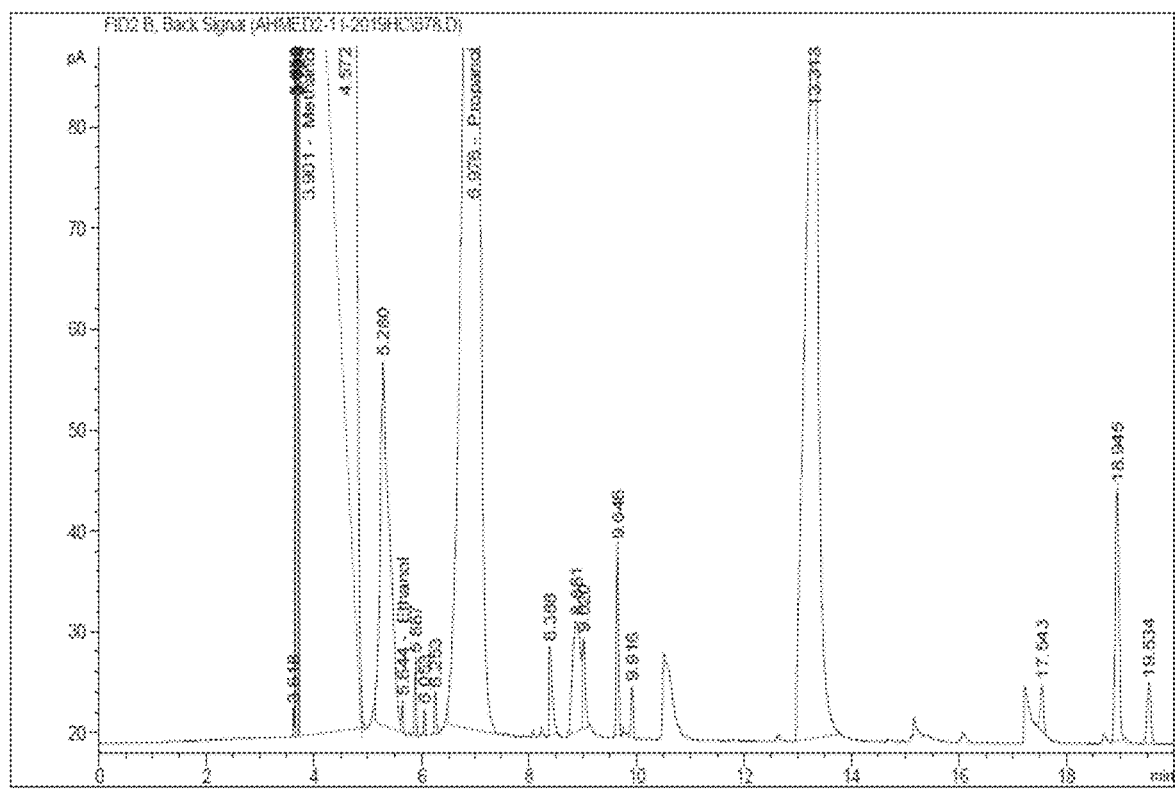
Figure 8B:
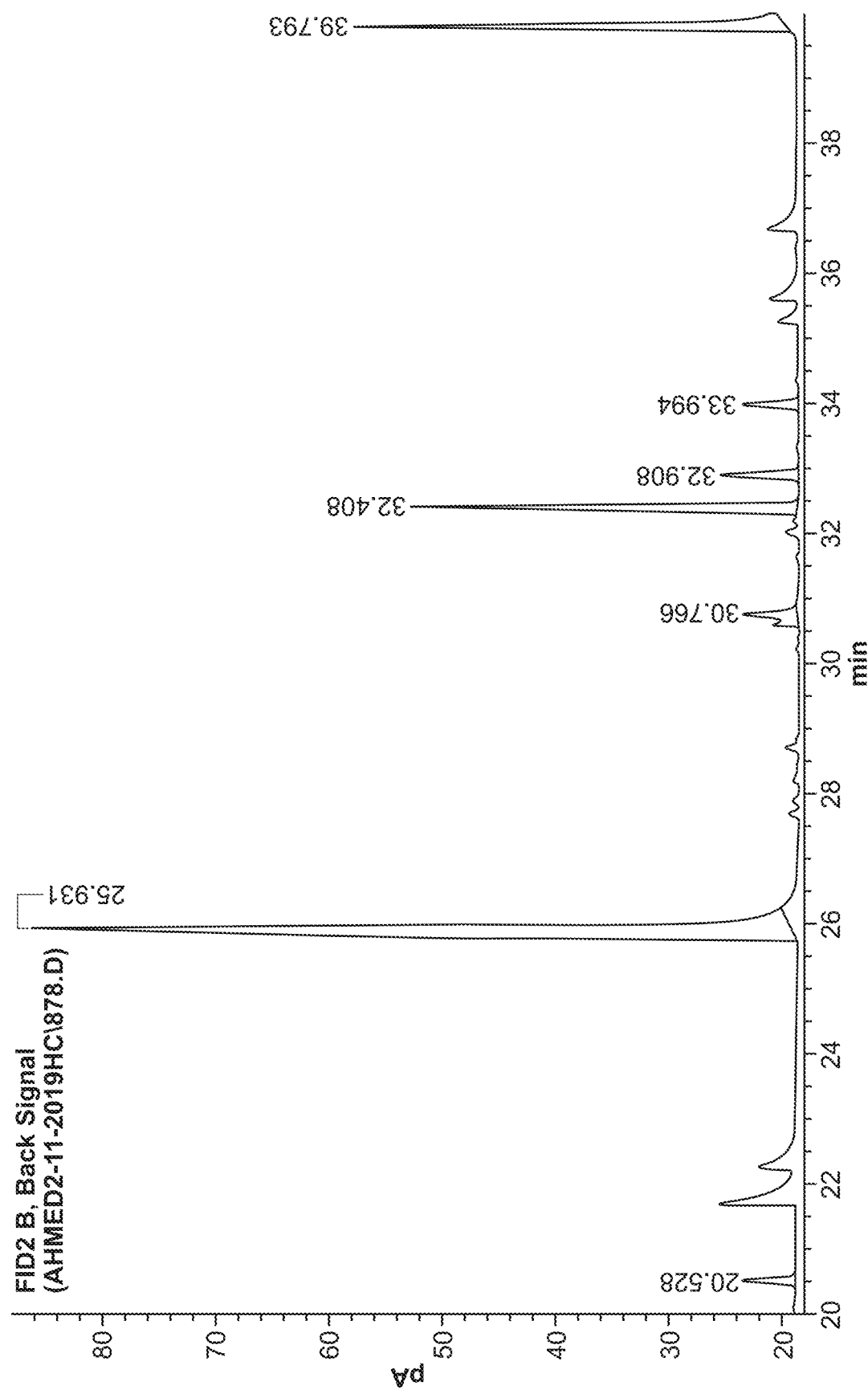
Figure 8C:
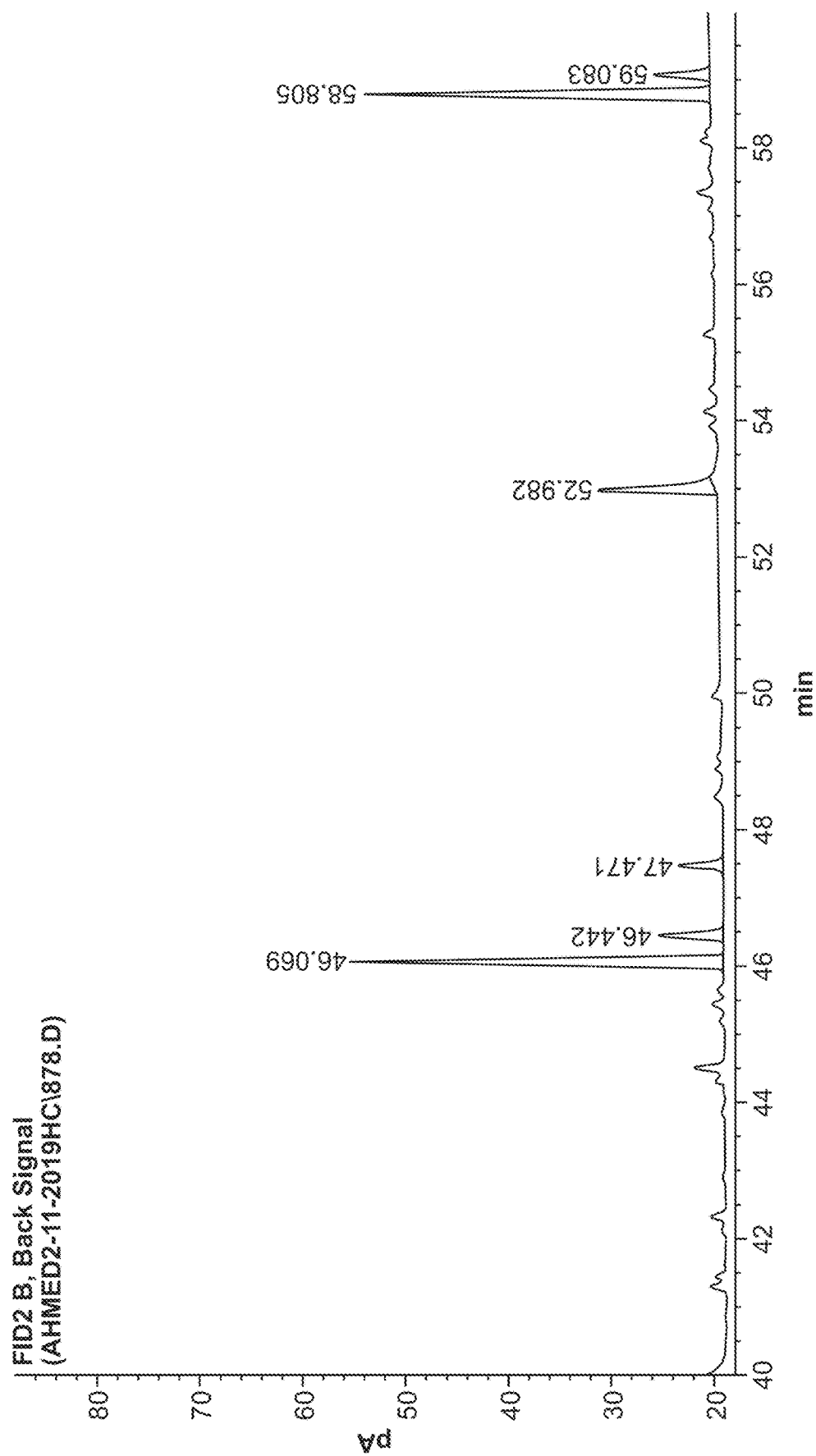
Figure 8D:
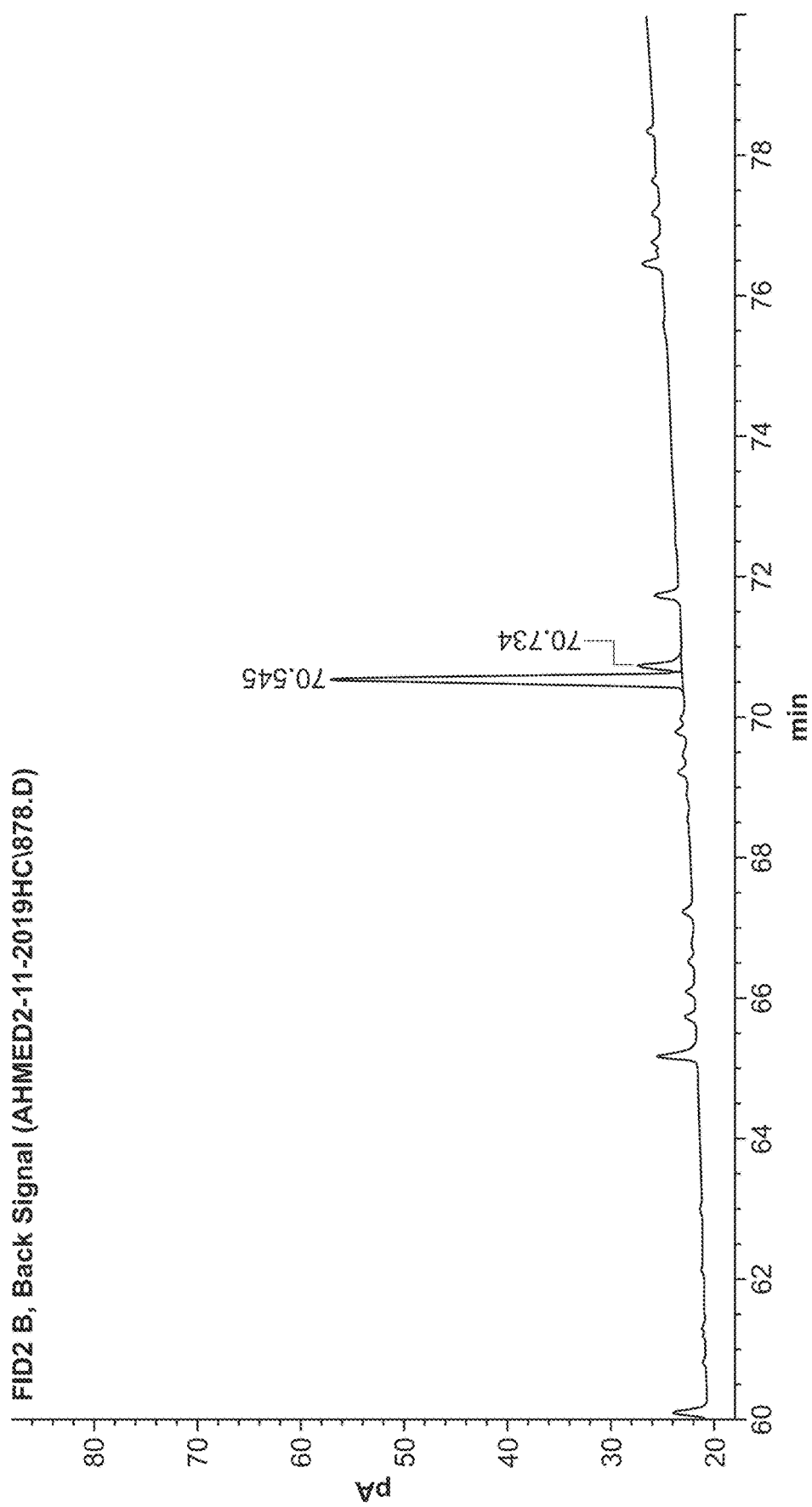
Figure 8E:
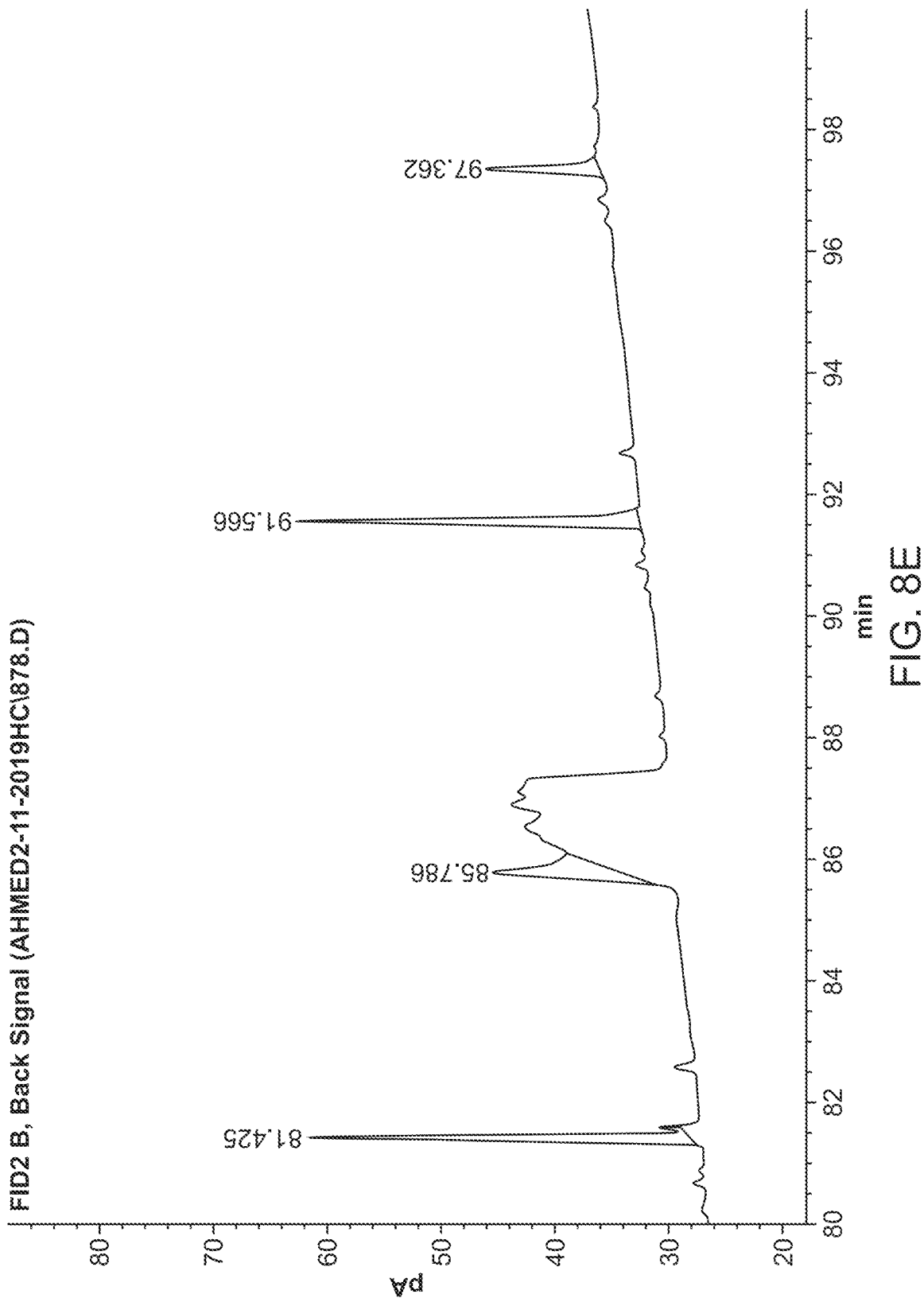
Figure 8F:
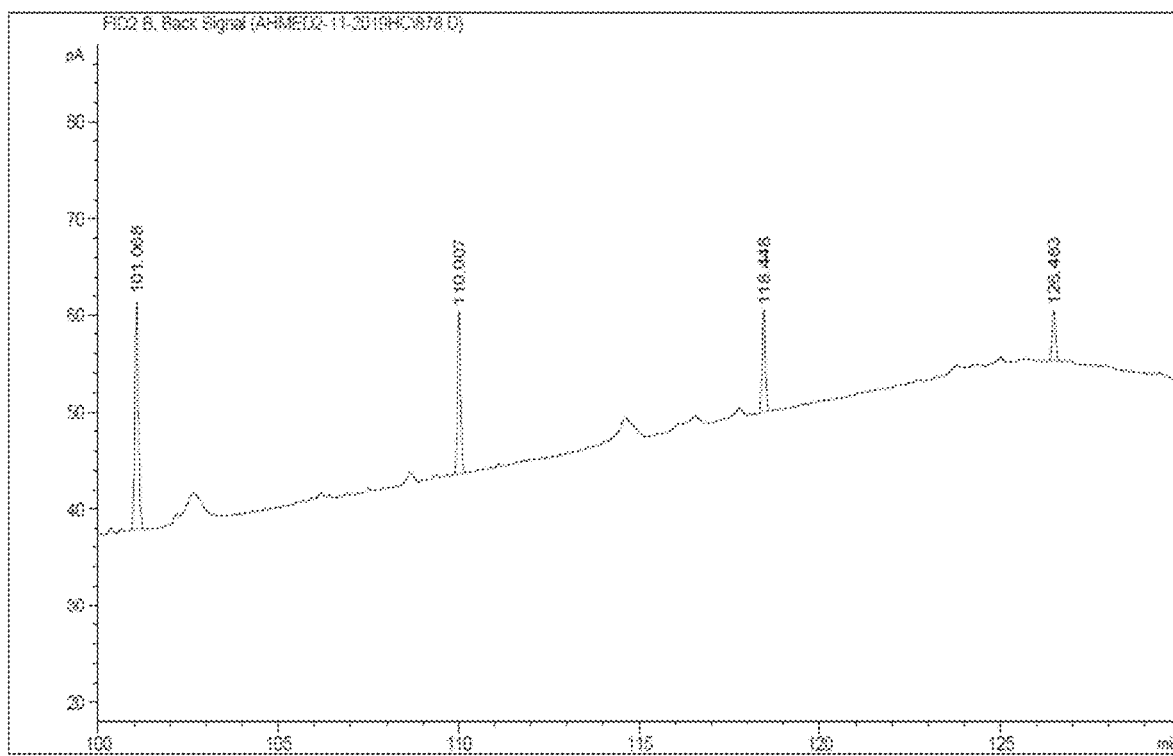
Figure 9A:
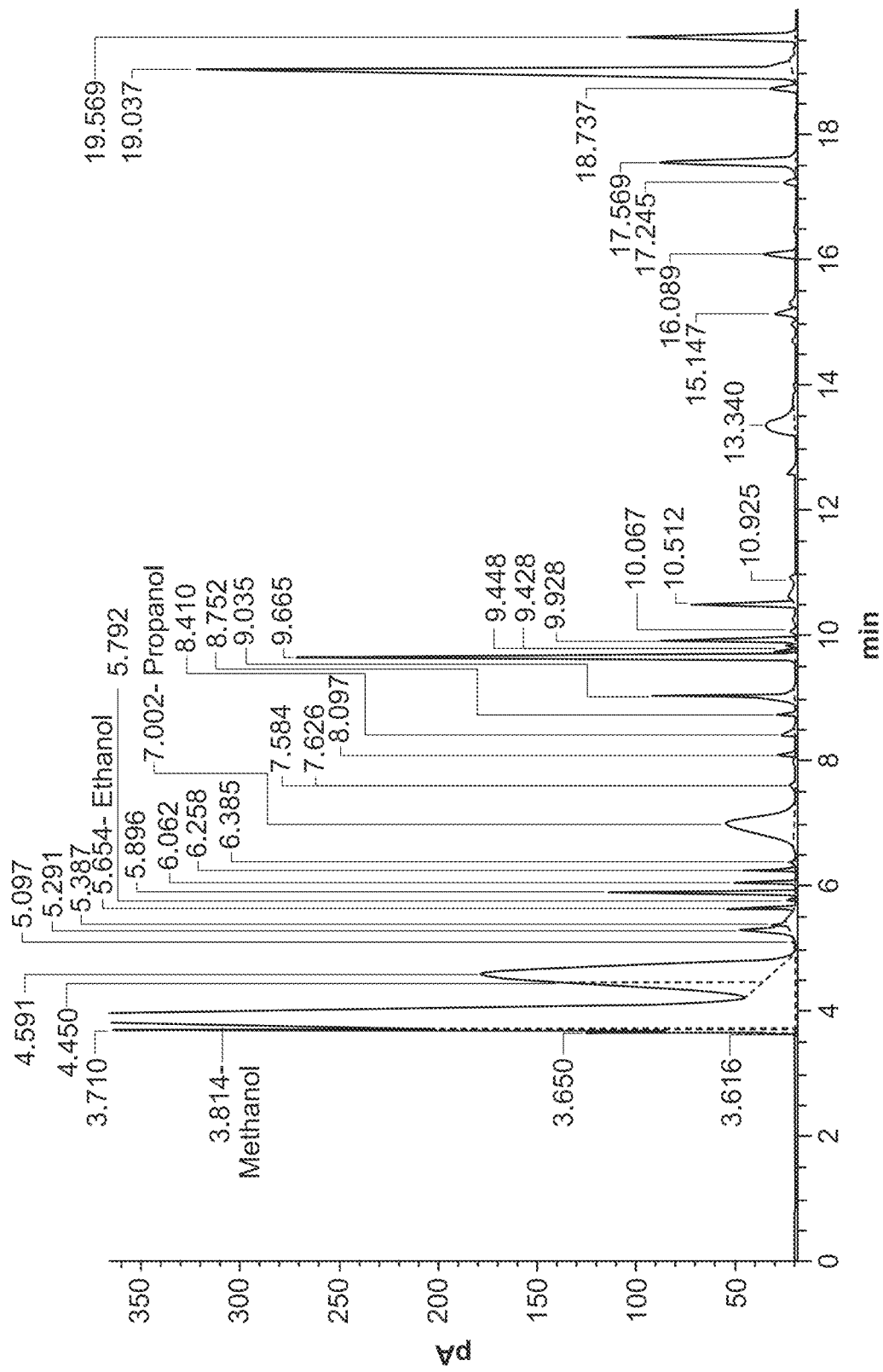
Figure 9B:
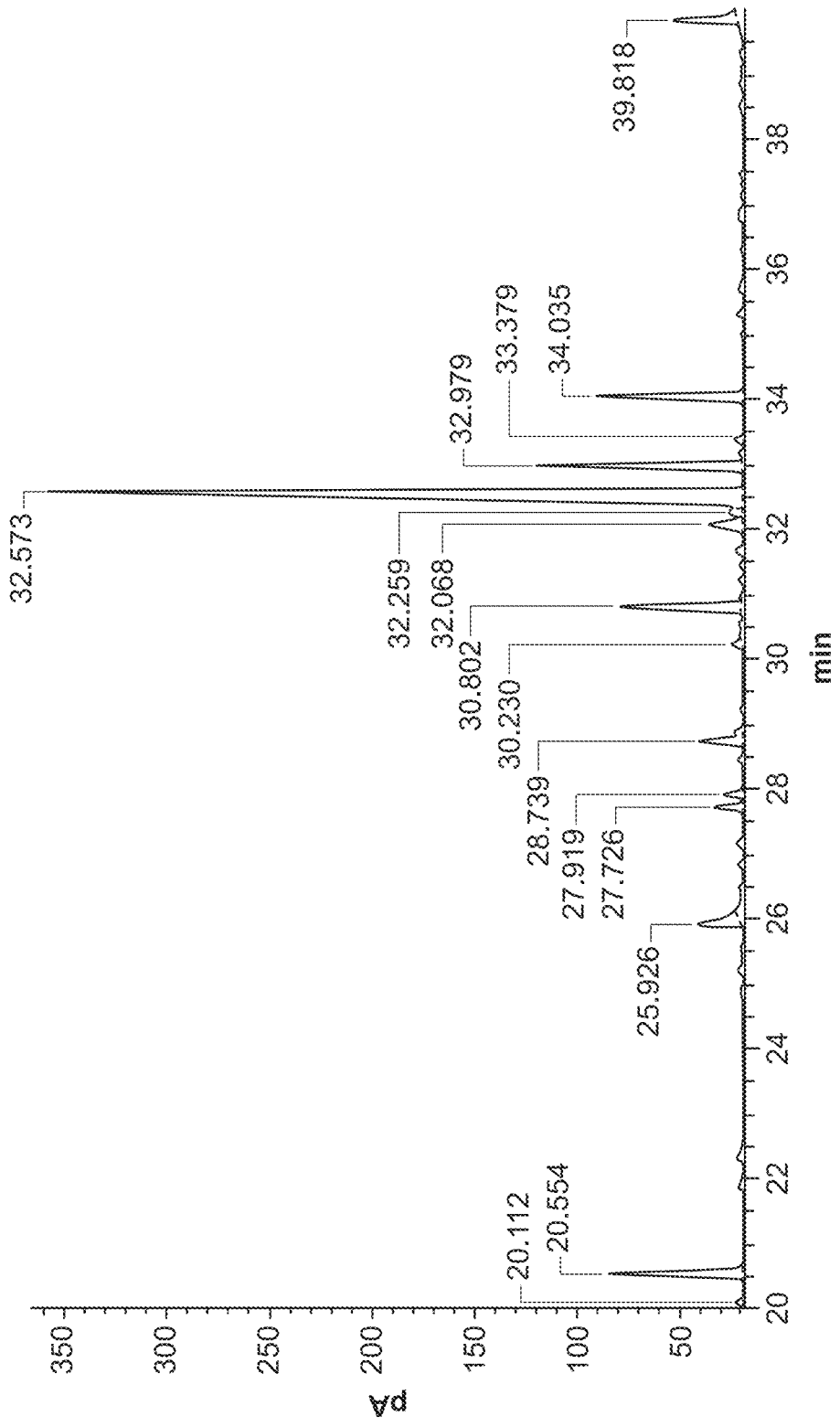
Figure 9C:
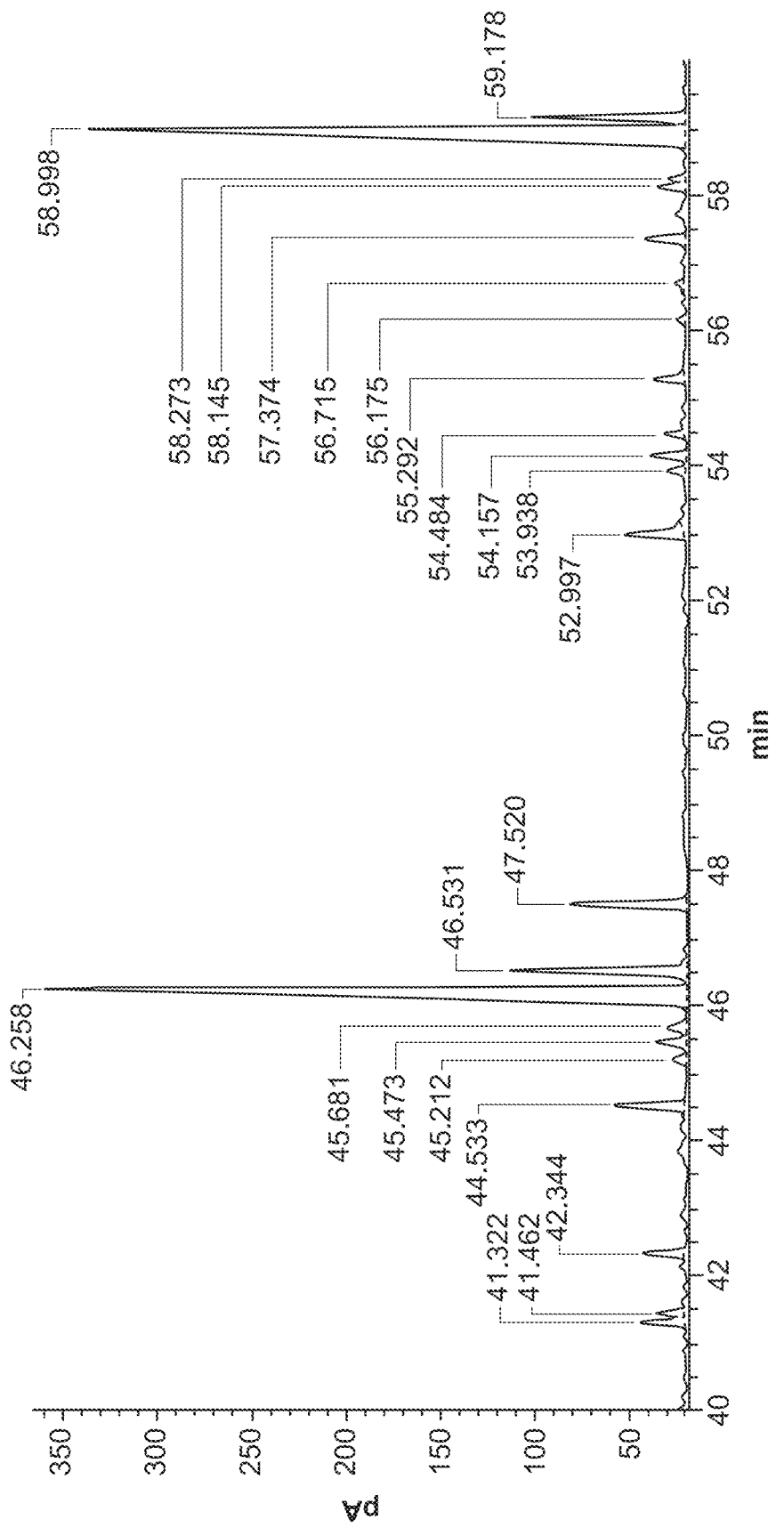
Figure 9D:
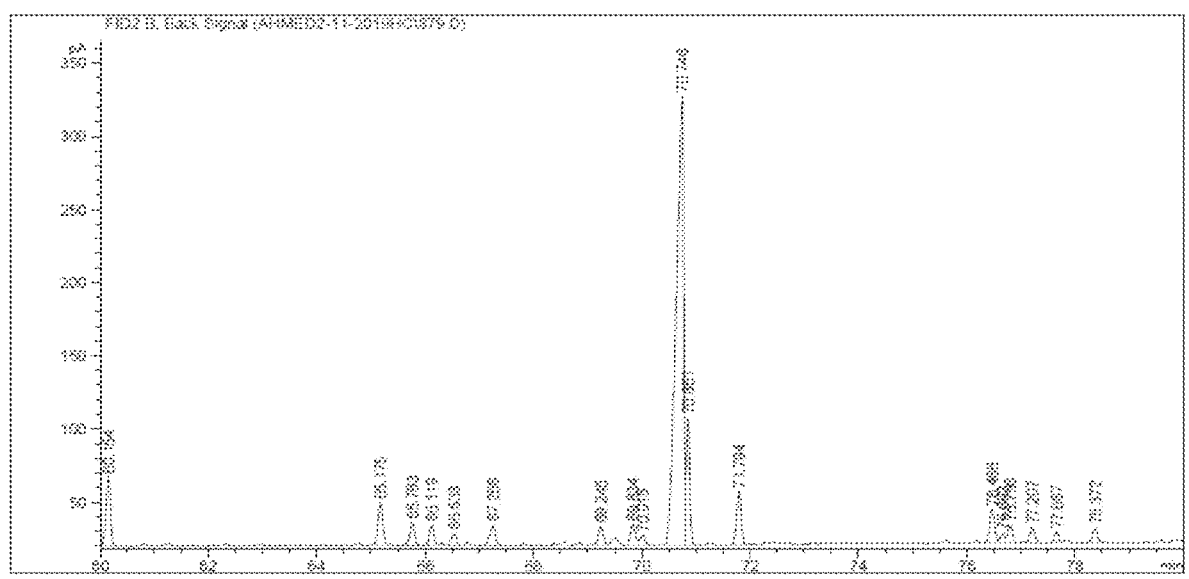
Figure 9E:
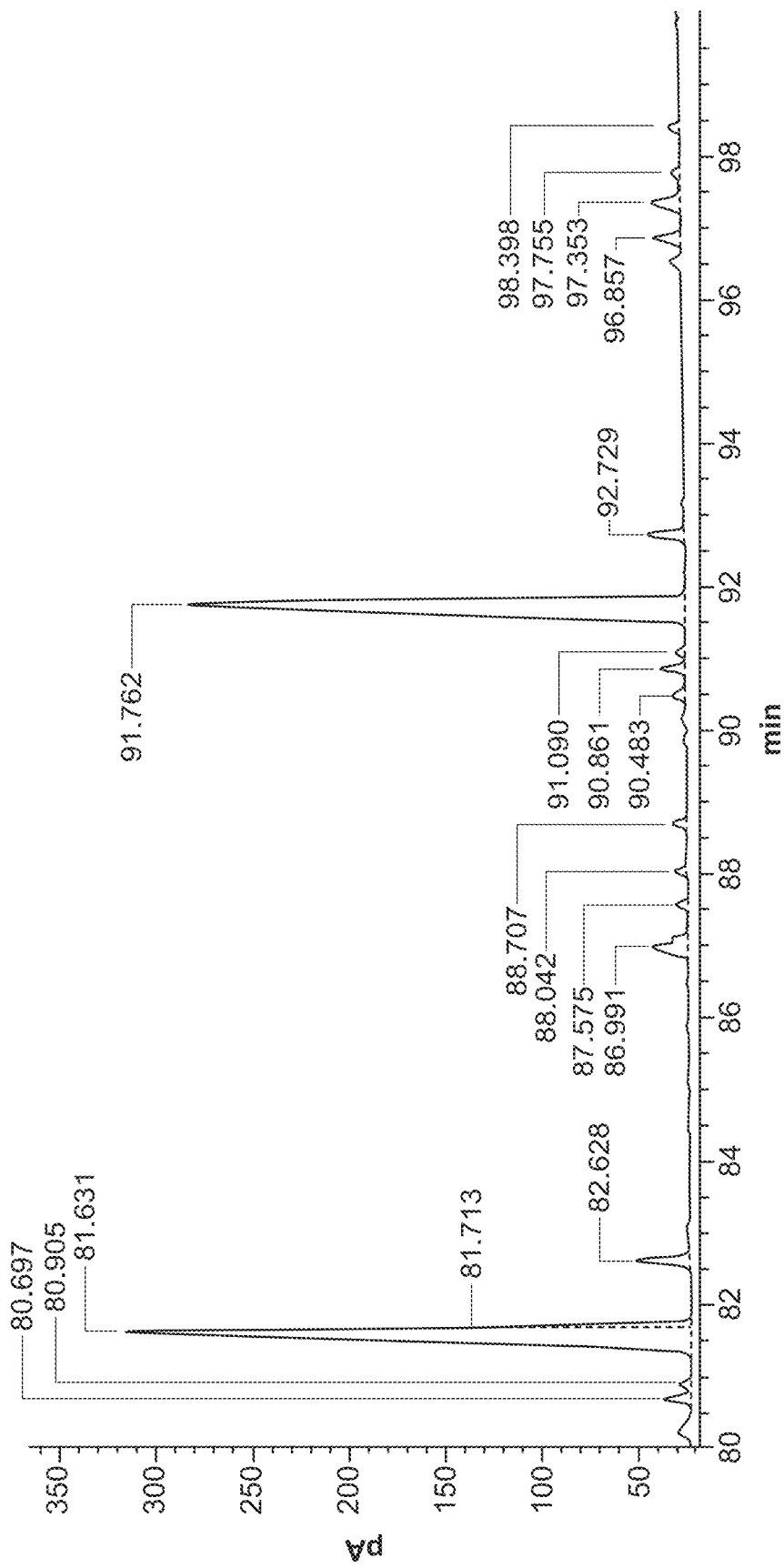
Figure 9F:
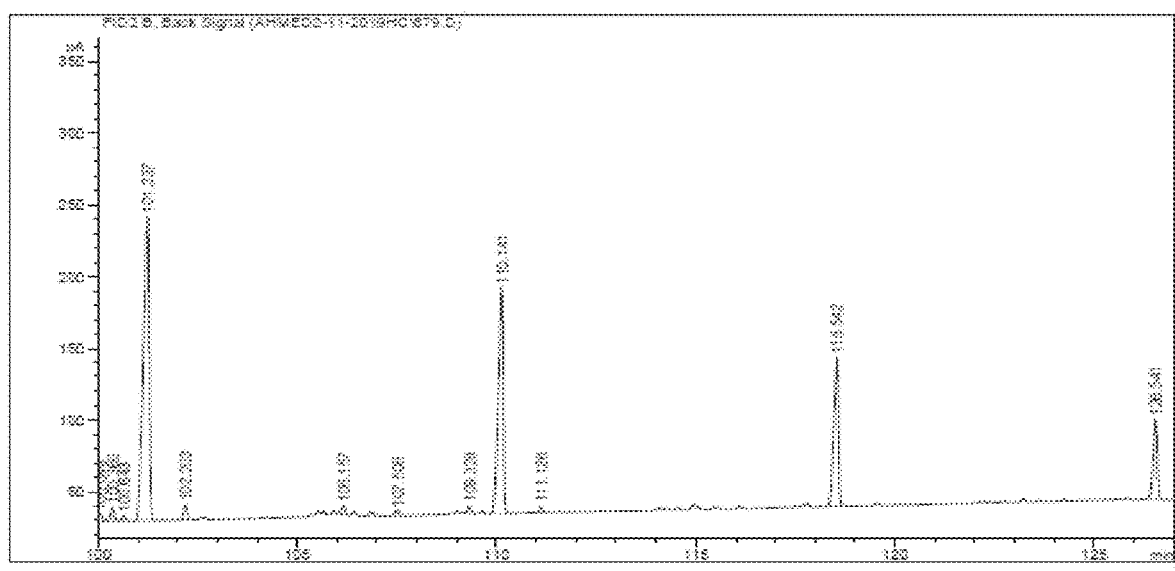

The high-resolution XPS spectra of $CuO_{(75)}/ZnO_{(15)}/Al_2O_{3(10)}$ including Cu2p ($2p_{3/2}$ and $2p_{1/2}$) with its corresponding 2 peaks of $Cu^0$ and 4 peaks of $Cu^{2+}$ (FIG. 7a), Zn2p ($2p_{3/2}$ and $2p_{1/2}$) with its 2 peaks for $Zn^0$ and $Zn^{2+}$ (FIG. 7b), and 2 peaks of O1s oxide/hydroxide (FIG. 7c). The observed higher oxidation states of Cu is attributed to its higher contents in the catalysts, while the 2 intense peaks of O 1s are due to the presence of dual hydroxide phase with the oxide.

FIG. 8 Gas chromatography and flame emission detection (GC-FID) analysis was carried out for the liquid products obtained using free-standing $CuO_{(40)}/ZnO_{(30)}/Al_2O_{3(30)}$ catalysts at 250° C. and under 50 bar. The catalytic performance of the as-synthesized catalysts were carried out for syngas conversion under differ temperatures and pressures. Both GC-FID and GC-MS chromatography tools were used to analyzed the obtained liquid products.

FIG. 8 shows the GC-FID analysis that was carried out for the liquid products obtained using $CuO_{(40)}/ZnO_{(30)}/Al_2O_{3(30)}$ catalysts at 250° C. and under 50 bar. The results showed the presence of wide ranges of heavy hydrocarbons from $C_5$ to $C_{25}$. The results showed the same hydrocarbon fuel products from $C_5$ to $C_{25}$ but with a higher yield compared to known freestanding catalyst.

Figure 10:
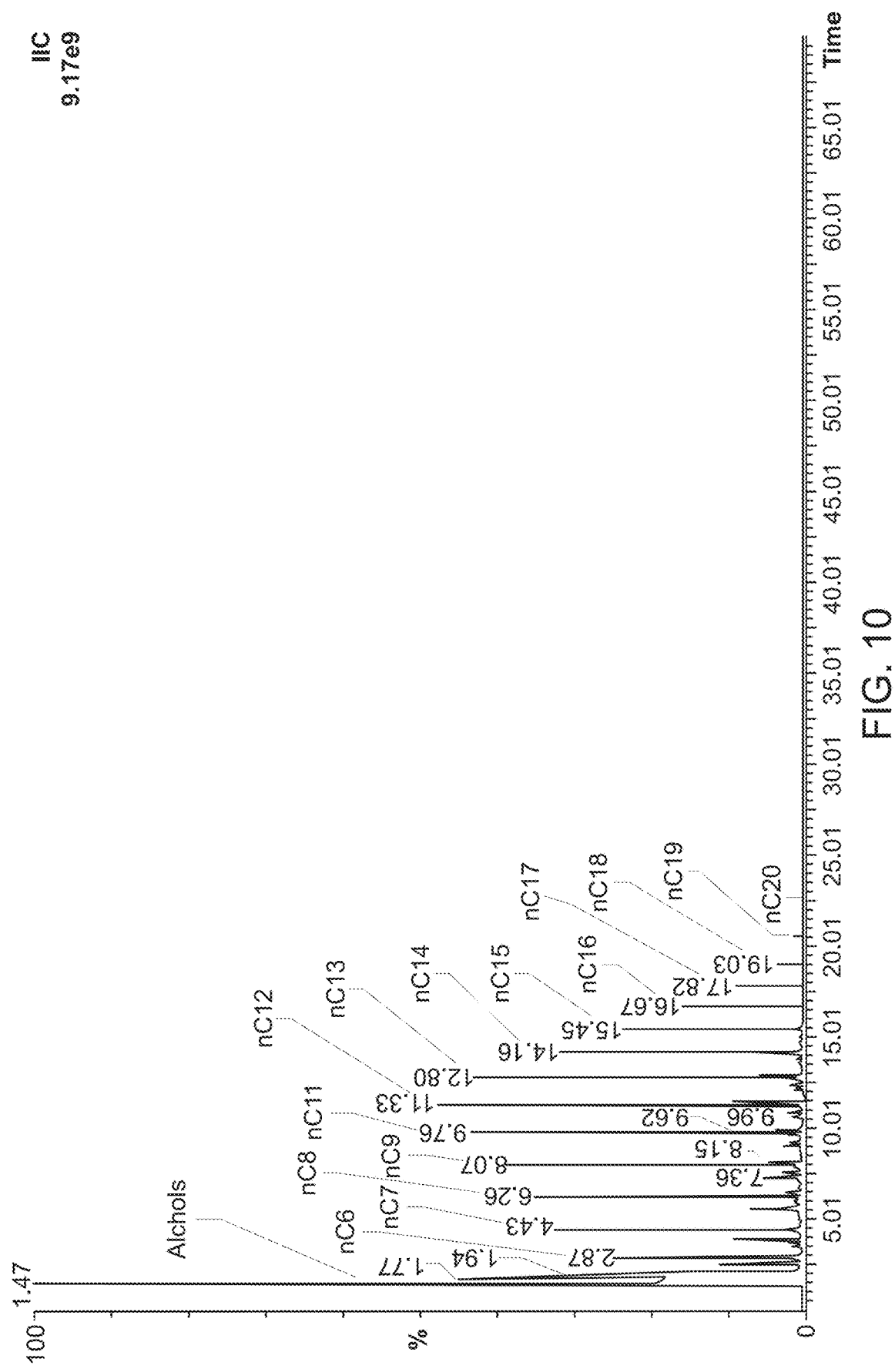
FIG. 10 shows GC-Ms analysis carried out for the liquid products obtained using $CuO_{(60)}/ZnO_{(30)}/Al_2O_{3(10)}$ supported on ZMS-5 catalysts at 250° C. and under 50 bar.
Figure 11:
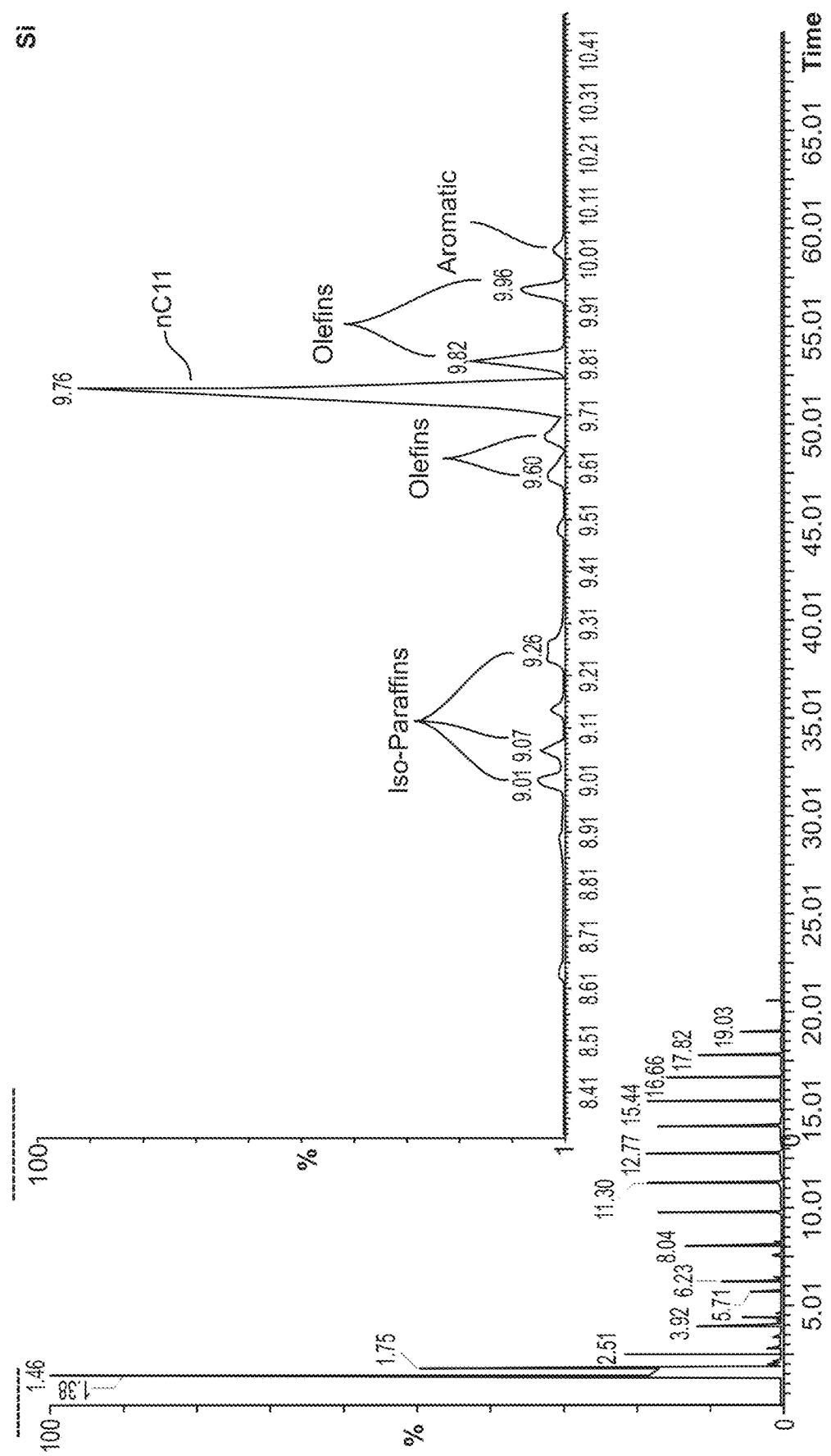
FIG. 11 shows GC-Ms analysis carried out for the liquid products obtained using $CuO_{(60)}/ZnO_{(30)}/Al_2O_{3(10)}$ supported on $Al_2O_3$ catalysts at 250° C. and under 50 bar. The insight shows the magnification of the area with respect to some hydrocarbons.

FIG. 10 shows the GC-Ms analysis that was carried out for the liquid products obtained using $CuO_{(60)}/ZnO_{(30)}/Al_2O_{3(10)}$ supported on ZMS-5 catalysts at 250° C. and under 50 bar. The results showed the fingerprint of the Fischer-Tropsch process products including the heavy hydrocarbon fuel products from $C_6$ to $C_{20}$ which were assigned to paraffin, olefins, and aromatic as well as their isomers. Surprisingly, a variety of alcohols, ranging from methanol to nonanol, along with their isomers, were observed. A wide ranges of parameters—including changing temperatures from 180 to 250° C., pressures from 10 to 70 bar, and different supports including $Al_2O_3$ and ZCS-M on the as-synthesized catalysts—were tested. The results showed the successful formation heavy hydrocarbons and alcohols with the fingerprint of FTs synthesis (FIGS. 8-21).

Prior to the instant disclosure, the conversion of syngas to usable heavy hydrocarbon fuels on metal-based catalysts required harsh reaction conditions including elevated temperatures and high pressures as well as high loading amount of metals. The instant Examples show that problems have been overcome by using a combination of the unique catalytic and electronic properties of multiple metal oxide supported catalysts. The as-synthesized Al oxide-supported Cu/Zn-oxide catalysts, not only allowed the efficient conversion of syngas to heavy liquid hydrocarbon fuels under ambient reaction conditions but also can be easily prepared from inexpensive and earth-abundant resources.

Table 1 shows a comparison between the catalysts set forth in the instant disclosure and those previously reported for Fischer-Tropsch synthesis:

| Ratio of $H_2$—CO | Catalytic system | Promoter | Synthesis Method | Pressure bar | Temperature ° C. | Products | Ref. |
|---|---|---|---|---|---|---|---|
| 2-0.5 | The instantly disclosed catalysts CuO/ZnO/$Al_2O_3$ | | One-pot combustion | 10-30 | 180-250 | $nC_4$-$nC_{24}$ Alcohols Methanol to nonanol | Our work |
| 2-0.7 | Pt—Re—Ru/ $SiO_2$ & $Al_2O_3$ | | | 12.1-30 | 270 | | See reference [1] |
| | Co—Ru—Ni/ silica & zeolite | | | 30 | 260 | | See reference [2] |
| 0.5-2.5 | Co—Pd—Ru— Pt/$SiO_2$ | K & Na | | 10 | 240 | | See reference [3] |
| 2 | Ru/Co—Co/ HZSM-5 | | impregnation method | 20 | 460c (H2) | | See reference [4] |
| 2 | Co—$SiO_2$/ SiC | | | 10-25 | 230-270 | | See reference [5] |
| patent | Fe—Co | | | | | | See reference [6] |
| | Co—Ni | | slurry impregnation | | | | See reference [7] |
| 2 | Co oxide | | | 20 | 230-250 | | See reference [8] |

-continued

| Ratio of H$_2$—CO | Catalytic system | Promoter | Synthesis Method | Pressure bar | Temperature ° C. | Products | Ref. |
|---|---|---|---|---|---|---|---|
| 2 | Co/TiO$_2$ | | | 20 | 220 | | See reference [9] |
| 2 | Co | | | 20-40 | 227 | | See reference [10] |
| 2 | Co | | | 20-40 | 200 | | See reference [11] |
| 2 | Co/TiO$_2$ | W and w/o | | 20 | 220 | | See reference [12] |
| 1 | Fe/Cu | Alkaline element | micro emulsion method | 17 | 290 | | See reference [13] |
| 2 | Fe—Co | | | 20-32 | 230-240 | | See reference [14] |
| 2 | Co | | | 20 | 230 | | See reference [15] |
| | Co—Fe/ Al$_2$O$_3$, SiO$_2$ | Pd, Pt, Re, and Ru | impregnation | 55 | 350 | | See reference [16] |
| 1-5 | Fe-ϒ Al$_2$O$_3$ | | impregnation | 10-20 | 320-380 | LOWER OLIFINES | See reference [17] |
| 0.5-4 | Fe—Co— Mo—Mn—Zr | | | 1-40 | 240-360 | LOWER OLIFINES | See reference [18] |
| 2 | Co/Al$_2$O$_3$— SiO$_2$ | | | 20 | 220-250 | | See reference [19] |
| 2 | Co/activate carbon | K, Ce & Zr | | 24 | 240 | C1-C20 | See reference [20] |
| 0.7-1 | Fe—Mg based | Cu | impregnation | 20 | 250 | | See reference [21] |
| 1-2 | Co—Mn | | | 5-20 | 240 | wax | See reference [22] |
| 1-2.4 | Co/SiO$_2$ | | | 21.6 | 210 | | See reference [23] |
| 1 | Fe/c | | | 10 | 350 | | See reference [25] |
| 2 | Pt—Co/SiO$_2$/ SiC | | impregnation | 20 | 220 | | |
| 2 | Co/SiO$_2$/ SBA | | | 20 | 210 | | See reference [26] |
| 2 | Co/ZSM-5 | | | 10 | 260 | | See reference [27] |
| 2 | Co/Al$_2$O$_3$ Co/MIL-53(Al) | | | 10 | 220 | | See reference [28] |
| 2 | Co—Pt/ SiO$_2$ | | | 10 | 210 | | See reference [29] |
| 2 | Co/ZSM-(1-15) | | | 10 | 220 | | See reference [30] |
| 2 | Ru/Al— SB-15 | | | 10 | 250 | | See reference [31] |
| 2 | Ru/Al— SB-15 | | | 10 | 230 | | See reference [32] |
| 1-2 | Ru/ SBA-15 | | | 10 | 235 | | See reference [33] |
| 2 | Co/TiO$_2$ | | | 10 | 210 | | See reference [34] |

-continued

| Ratio of $H_2$—CO | Catalytic system | Promoter | Synthesis Method | Pressure bar | Temperature ° C. | Products | Ref. |
|---|---|---|---|---|---|---|---|
| | Pt/Al$_2$O$_3$ | | | 19 | 220 | | See reference [35] |
| | Patent comparison | | | | | | See reference [36] |

The following provide background information:
1. Shafer, W. D., et al., Fischer-Tropsch: Product Selectivity—The Fingerprint of Synthetic Fuels. 2019. 9(3): p. 259.
2. Sadek, R., et al., Cobalt Based Catalysts Supported on Two Kinds of Beta Zeolite for Application in Fischer-Tropsch Synthesis. 2019. 9(6): p. 497.
3. Jahangiri, H., et al., A review of advanced catalyst development for Fischer-Tropsch synthesis of hydrocarbons from biomass derived syn-gas. 2014. 4(8): p. 2210-2229.
4. Wang, S., et al., Improved Fischer-Tropsch synthesis for gasoline over Ru, Ni promoted Co/HZSM-5 catalysts. 2013. 108: p. 597-603.
5. Riyahin, M., et al., Optimization of reaction condition on the product selectivity of Fischer-Tropsch synthesis over a Co—SiO2/SiC catalyst using a fixed bed reactor. 2017. 35(11): p. 1078-1084.
6. Walsh, R. N., et al., Fischer-Tropsch synthesis. 2019, Google Patents.
7. van Helden, P., et al., Cobalt-nickel bimetallic Fischer-Tropsch catalysts: A combined theoretical and experimental approach. 2020. 342: p. 88-98.
8. Bae, J. W. and C. I. AHN, Mesoporous cobalt-metal oxide catalyst for Fischer-Tropsch synthesis reactions and a preparing method thereof 2018, Google Patents.
9. van Deelen, T. W., et al., Preparation of Cobalt nanocrystals supported on metal oxides to study particle growth in Fischer-Tropsch catalysts. 2018. 8(11): p. 10581-10589.
10. Böller, B., K. M. Durner, and J. Wintterlin, The active sites of a working Fischer-Tropsch catalyst revealed by operando scanning tunnelling microscopy. Nature Catalysis, 2019. 2(11): p. 1027-1034.
11. Mahmoudi, H., et al., A review of Fischer Tropsch synthesis process, mechanism, surface chemistry and catalyst formulation. 2017. 2(1): p. 11-31.
12. Eschemann, T. O., J. Oenema, and K. P. J. C. T. de Jong, Effects of noble metal promotion for Co/TiO2 Fischer-Tropsch catalysts. 2016. 261: p. 60-66.
13. Zamani, Y., et al., Effect of Calcium Promoters on Nanostructured Iron Catalyst for Fischer-Tropsch Synthesis. 2015. 5(1): p. 21-27.
14. Calderone, V. R., et al., De novo design of nanostructured iron-cobalt Fischer-Tropsch catalysts. 2013. 52(16): p. 4397-4401.
15. Lok, C. M., Novel highly dispersed cobalt catalysts for improved Fischer-Tropsch productivity, in Studies in surface science and catalysis. 2004, Elsevier. p. 283-288.
16. Yunes, S., et al., Effect of High Pressure on the Reducibility and Dispersion of the Active Phase of Fischer-Tropsch Catalysts. 2019. 12(12): p. 1915.
17. De Jong, K. P., A. Koeken, and M. Ruitenbeek, Fischer-Tropsch process for converting synthesis gas to a lower olefin. 2015, Google Patents.
18. Tones Galvis, H. M. and K. P. J. A. c. de Jong, Catalysts for production of lower olefins from synthesis gas: a review. 2013. 3(9): p. 2130-2149.
19. Van de Loosdrecht, J., et al., Fischer-Tropsch synthesis: catalysts and chemistry, in Comprehensive Inorganic Chemistry II: from elements to applications. 2013, Elsevier. p. 525-557.
20. Ma, W.-P., et al., Fischer-Tropsch Synthesis over Activated-Carbon-Supported Cobalt Catalysts: Effect of Co Loading and Promoters on Catalyst Performance. 2004. 43(10): p. 2391-2398.
21. Al-Dossary, M., et al., Cu-promoted Fe2O3/MgO-based Fischer-Tropsch catalysts of biomass-derived syngas. 2015. 54(3): p. 911-921.
22. Enger, B. C., et al., Effects of Sulphur on a Co/Mn-based Catalyst for Fischer-Tropsch Reactions. 2018. 148(10): p. 2980-2991.
23. Das, T. K., et al., Fischer-Tropsch synthesis: Kinetics and effect of water for a Co/SiO2 catalyst. 2005. 19(4): p. 1430-1439.
24. Lyu, S., et al., Structural evolution of carbon in an Fe@C catalyst during the Fischer-Tropsch synthesis reaction. 2019. 9(4): p. 1013-1020.
25. Davis, B. H. and M. L. Occelli, Fischer-Tropsch Synthesis: Comparisons of SiO2- and SiC-Supported Co Catalysts Prepared through Aqueous Impregnation and CVD Methods, in Fischer-Tropsch Synthesis, Catalysts, and Catalysis. 2016, CRC Press. p. 74-103.
26. Zhao, Y., et al., SBA-16-Supported Cobalt Catalyst with High Activity and Stability for Fischer-Tropsch Synthesis. 2012. 4(2): p. 265-272.
27. Wei, L., et al., Fischer-Tropsch Synthesis Bifunctional Catalysts: Cobalt Supported on 3D Mesoporous Cellular Silica Foams Assembled by Using ZSM-5 Seeds. 2017. 9(20): p. 3895-3903.
28. Sun, B., et al., Novel Cobalt Catalysts Supported on Metal-Organic Frameworks MIL-53 (Al) for the Fischer-Tropsch Synthesis. 2019. 7(4): p. 1800802.
29. Liu, C., et al., Promotion effects of plasma treatment on silica supports and catalyst precursors for cobalt Fischer-Tropsch catalysts. 2016. 6(62): p. 57701-57708.
30. Chen, S., et al., ZSM-5 seed-grafted SBA-15 as a high performance support for cobalt Fischer-Tropsch synthesis catalysts. 2015. 5(11): p. 4985-4990.
31. Chen, S., et al., Ru catalysts supported on Al-SBA-15 with high aluminum content and their bifunctional catalytic performance in Fischer-Tropsch synthesis. 2014. 4(4): p. 1005-1011.
32. Chen, S., et al., Effect of tetrahedral aluminum on the catalytic performance of Al-SBA-15 supported Ru catalysts in Fischer-Tropsch synthesis. 2013. 3(4): p. 1063-1068.
33. Xiong, H., et al., Preparation and catalytic activity for Fischer-Tropsch synthesis of Ru Nanoparticles confined in the channels of mesoporous SBA-15. 2008. 112(26): p. 9706-9709.

34. Liu, C., et al., Effect of TiO2 Surface Engineering on the Performance of Cobalt-Based Catalysts for Fischer-Tropsch Synthesis. 2018. 58(2): p. 1095-1104.
35. Kizilkaya, A. C., et al., Effect of ammonia on cobalt Fischer-Tropsch synthesis catalysts: a surface science approach. 2019. 9(3): p. 702-710.
36. Oukaci, R., A. H. Singleton, and J. G. J. A. C. A. G. Goodwin Jr, Comparison of patented Co F-T catalysts using fixed-bed and slurry bubble column reactors. 1999. 186(1-2): p. 129-144.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A composition comprising CuO and ZnO on $Al_2O_3$, wherein the composition comprises:
   35 to 80 percent by mole CuO;
   10 to 35 percent by mole ZnO; and
   5 to 35 percent by mole $Al_2O_3$;
   wherein the total percent by mole of Cu, ZnO, and $Al_2O_3$ is 100; wherein the composition is on a support selected from aluminum oxide, zeolite, a metal oxide, carbon, a carbon-based support, graphene, graphene-based support, and a metal organic framework support.

2. The composition of claim 1, wherein the composition comprises:
   40 percent by mole CuO;
   30 percent by mole ZnO; and
   30 percent by mole $Al_2O_3$.

3. The composition of claim 1, wherein the composition comprises:
   60 percent by mole CuO;
   30 percent by mole ZnO; and
   10 percent by mole $Al_2O_3$.

4. The composition of claim 1, wherein the composition comprises:
   75 percent by mole CuO;
   15 percent by mole ZnO; and
   10 percent by mole $Al_2O_3$.

5. The composition of claim 1, wherein the nanoparticles have an average diameter of 30 nm.

6. The composition of claim 1, wherein the composition is characterized by amorphous aggregated oxide particles.

7. The composition of claim 6, wherein the amorphous aggregated oxide particles have an average diameter of 400-800 nm.

8. The composition claim 1, wherein the composition is free of any impurities as determined by x-ray photo-electron spectroscopy.

9. The composition of claim 1, wherein the elements Cu, Zn, and Al are evenly distributed.

10. The composition of claim 1, wherein the atomic content of Cu, Zn, Al, and O is 8.68, 5.05, 18.86, and 63.77 respectively.

11. The composition of claim 1, wherein the atomic content of Cu, Zn, Al, and O is 13.62, 9.09, 11.47, and 62.95 respectively.

12. A process for making CuO/ZnO supported on $Al_2O_3$ comprising:
   a. combusting metal precursors, glycine and water to form a powder; and
   b. annealing the powder;
   c. wherein the metal precursors are selected from the group consisting of $Cu(NO_3)_2$ or $Cu(OH)_2$, $Zn(NO_3)_2$ or ZnO, and $Al(NO_3)_2$ or $Al(OH)_3$.

13. The process of claim 12, wherein the combusting occurs at 420° C. until the water is removed and ignition occurs.

14. The process of claim 12, wherein the annealing occurs at 600° C.

15. A process for converting syngas into usable liquid $nC_4$-$nC_{25}$ hydrocarbons and $nC_1$-$nC_9$ alcohols, comprising contacting syngas to a composition, under syngas reaction conditions including $H_2$/CO syngas with a feeding rate ratio of 2/0.5 at 150-250° C. under pressure of 10-70 bar, of any one of the compositions of claims 1, 2-4, and 5-11 or a composition made by the process of claim 12-14; wherein the process produces liquid hydrocarbons using $CuO_{(40)}/ZnO_{(30)}/Al_2O_{3(30)}$, $CuO_{(60)}/ZnO_{(30)}/Al_2O_{3(10)}$, and $CuO_{(75)}/ZnO_{(15)}/Al_2O_{3(10)}$ catalysts.

16. The process of claim 15, wherein the contacting occurs at 150° C., 200° C., or 250° C.

17. The process of claim 15, wherein during the contacting, the $H_2$/CO feeding ratio is from 0.05 to 2.

18. The process of claim 15, wherein the process produces liquid alcohols at pressure $\geq 50$ bar and $\leq 70$ bar and at a temperature $\geq 200°$ C. and $\leq 250°$ C. using $CuO_{(40)}/ZnO_{(30)}/Al_2O_{3(30)}$, $CuO_{(60)}/ZnO_{(30)}/Al_2O_{3(10)}$, and $CuO_{(75)}/ZnO_{(15)}/Al_2O_{3(10)}$ catalysts.

19. The process of claim 15, wherein the process produces a combination of liquid hydrocarbons and alcohols using $CuO_{(40)}/ZnO_{(30)}/Al_2O_{3(30)}$, $CuO_{(60)}/ZnO_{(30)}/Al_2O_{3(10)}$, and $CuO_{(75)}/ZnO_{(15)}/Al_2O_{3(10)}$ catalysts under pressure 10-70 bar at a temperature 150-250° C.

* * * * *